United States Patent
Lairson et al.

(10) Patent No.: US 11,998,602 B2
(45) Date of Patent: Jun. 4, 2024

(54) METHODS FOR PROMOTING MYELINATION AND FOR TREATING DEMYELINATING DISEASES

(71) Applicant: The Scripps Research Institute, La Jolla, CA (US)

(72) Inventors: Luke Lairson, San Diego, CA (US); Brittney Beyer, San Diego, CA (US); Mingliang Fang, Singapore (SG); Gary Siuzdak, Cardiff, CA (US)

(73) Assignee: The Scripps Research Institute, La Jolla, CA (US)

( * ) Notice: Subject to any disclaimer, the term of this patent is extended or adjusted under 35 U.S.C. 154(b) by 834 days.

(21) Appl. No.: 16/978,558

(22) PCT Filed: Nov. 13, 2018

(86) PCT No.: PCT/US2018/060793
§ 371 (c)(1),
(2) Date: Sep. 4, 2020

(87) PCT Pub. No.: WO2019/172969
PCT Pub. Date: Sep. 12, 2019

(65) Prior Publication Data
US 2021/0023218 A1   Jan. 28, 2021

Related U.S. Application Data

(60) Provisional application No. 62/640,151, filed on Mar. 8, 2018.

(51) Int. Cl.
| | |
|---|---|
| *A61K 31/40* | (2006.01) |
| *A61K 31/5415* | (2006.01) |
| *A61K 45/06* | (2006.01) |
| *A61P 25/00* | (2006.01) |
| *C07C 303/02* | (2006.01) |
| *C07K 16/28* | (2006.01) |

(52) U.S. Cl.
CPC .............. *A61K 45/06* (2013.01); *A61P 25/00* (2018.01); *C07C 303/02* (2013.01); *C07K 16/286* (2013.01)

(58) Field of Classification Search
CPC .... A61K 31/40; A61K 31/5415; A61K 45/06; A61P 25/00; C07C 303/02; C07K 16/286
See application file for complete search history.

(56) References Cited

U.S. PATENT DOCUMENTS

2014/0038949 A1\*  2/2014  Schultz ................ A61K 31/135
                                                                514/304

OTHER PUBLICATIONS

Beyer et al. Metabolomics-based discovery of a metabolite that enhances oligodendrocyte maturation. Nature Chemical Biology, vol. 14, 22-34. (Year: 2018).\*

\* cited by examiner

Primary Examiner — Sikarl A Witherspoon
(74) Attorney, Agent, or Firm — Hugh Wang; Thomas Fitting

(57) ABSTRACT

This invention provides novel methods for treating or ameliorating symptoms of demyelinating diseases such as multiple sclerosis. The methods involve administering to subjects in need of treatment a pharmaceutical composition that contains a therapeutically effective amount of taurine and also a compound that induces oligodendrocyte precursor cell (OPC) differentiation (e.g., T3, benztropine, clemastine or miconazole). Some of the methods additionally involve administration to the subject a known agent for treating demyelinating diseases (e.g., SIP receptor agonists) or a known disease modifying drug. The invention also provides methods for increasing myelination and methods for promoting OPC differentiation into oligodendrocytes. These methods entail contacting a population of OPCs with a combination of taurine and a known OPC differentiation-inducing agent such as T3, clemastine, benztropine or miconazole.

20 Claims, 18 Drawing Sheets

Fig. 1
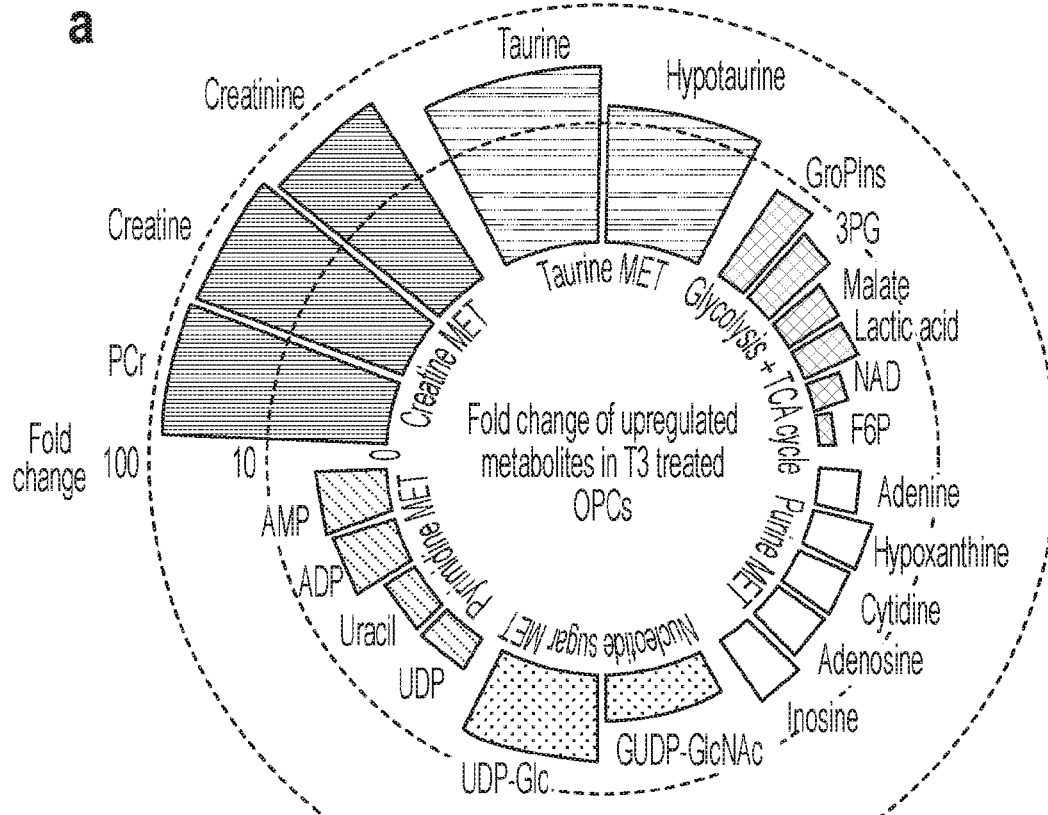
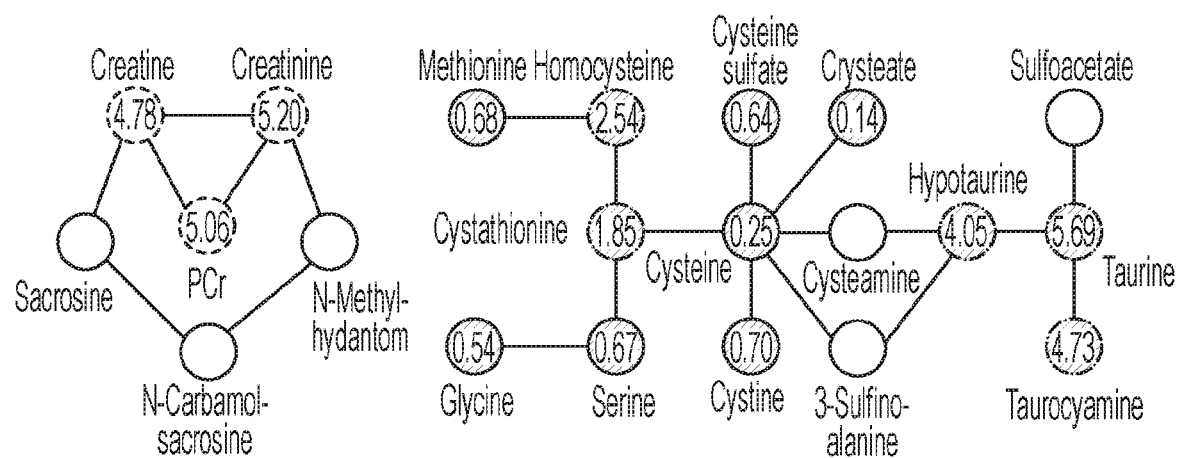
Fig. 1b

Fig. 2
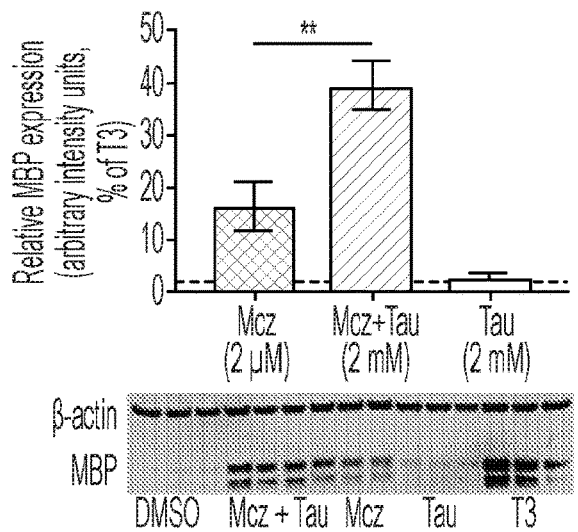 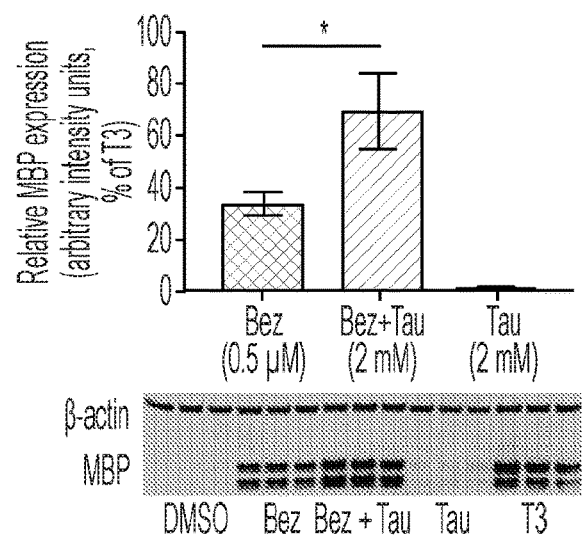
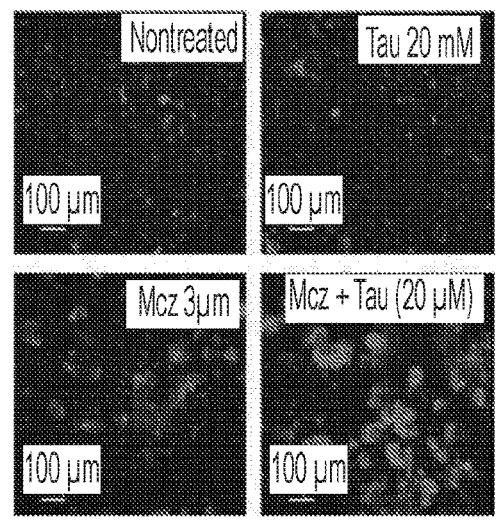 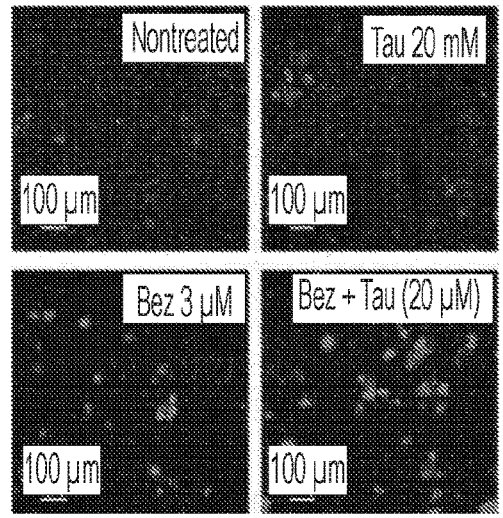
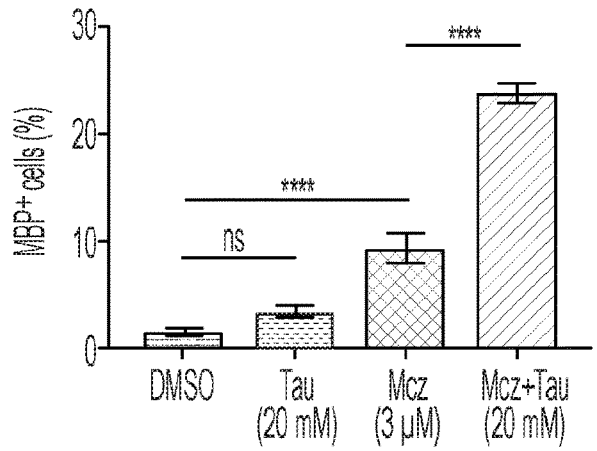 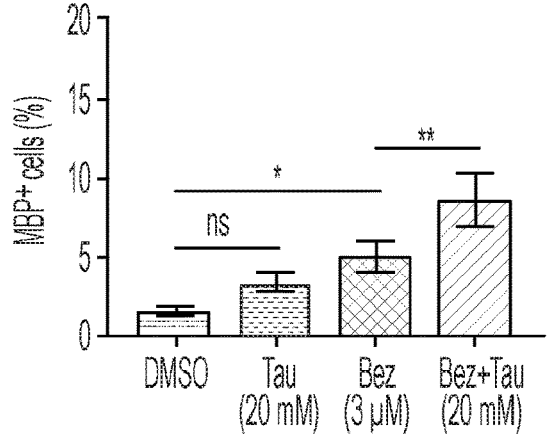

Fig. 5 a

D3 T3 vs. T3 + Tau

Serine (17.1) — Homocysteine (1.4)
    |
Cystathionine
    |
Cysteine (58.8) — (0.5) Glutamate
    |           \
Cysteamine    Glutamyl-cysteine — (1.8) GSH
    |
(2.4) Hypotaurine
    |
(35.1) Taurine D6 T3 vs. T3 + Tau Serine (2.1) — Homocysteine (2.6)
    |
Cystathionine
    |
Cysteine (26.6) — (2.2) Glutamate
    |           \
Cysteamine    Glutamyl-cysteine — (6.1) GSH
    |
(1.5) Hypotaurine
    |
(11.6) Taurine

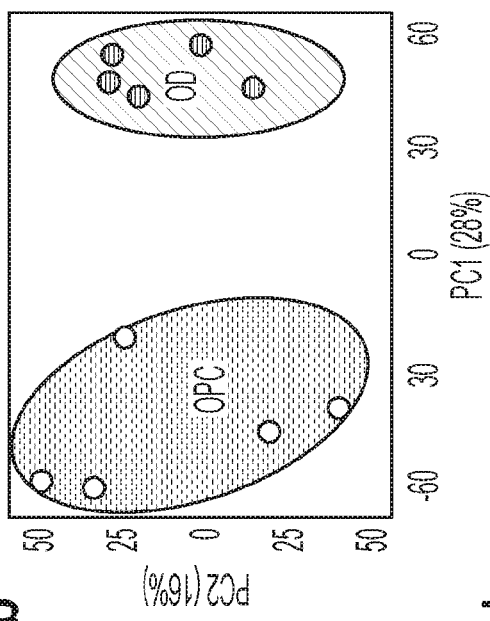
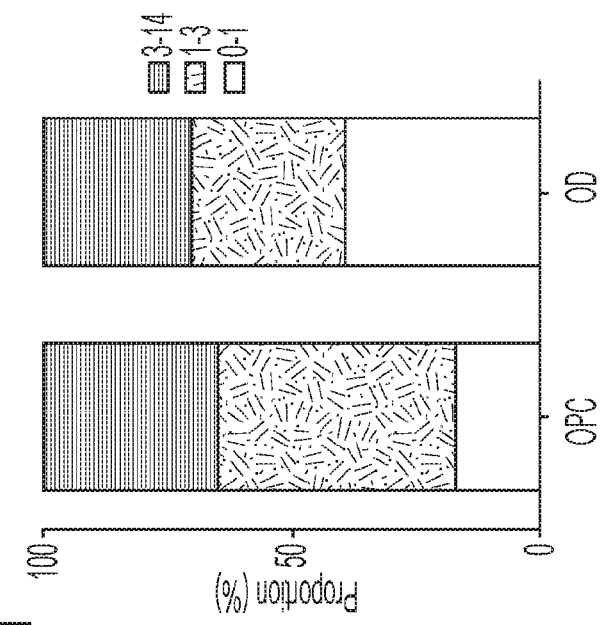
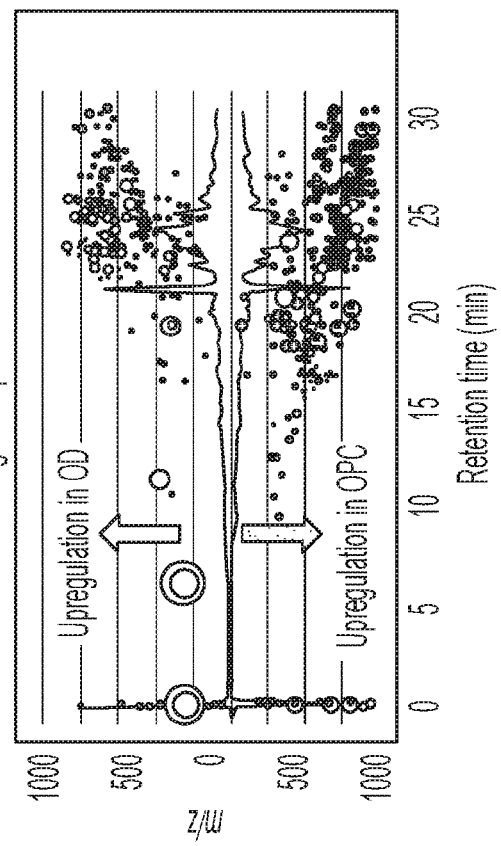
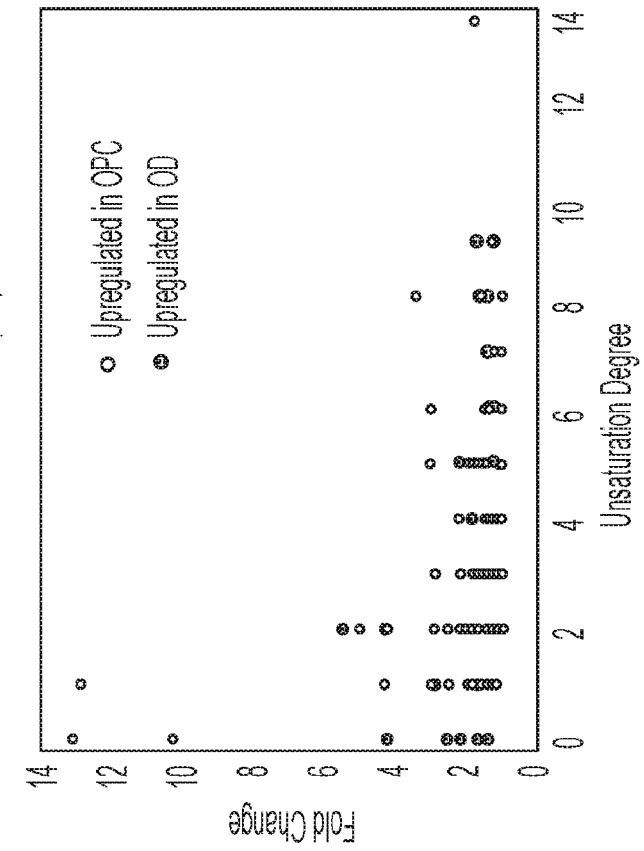
Fig. 7

Fig. 9
a
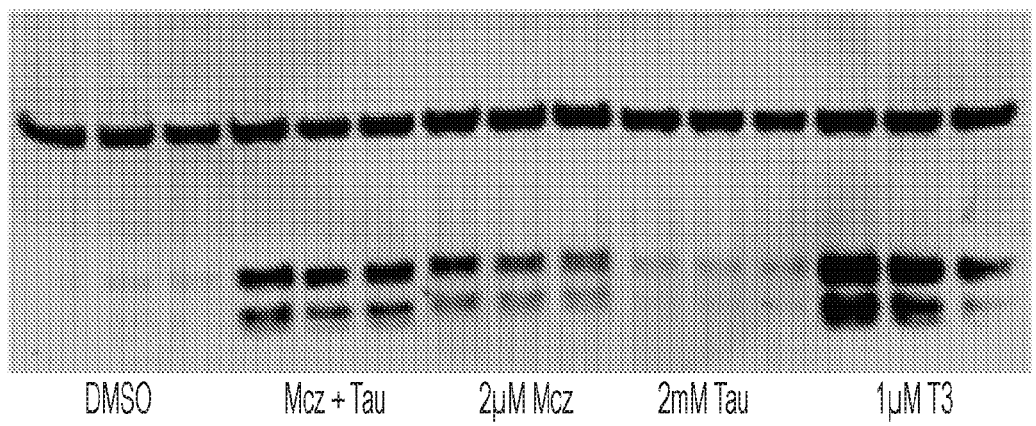
c
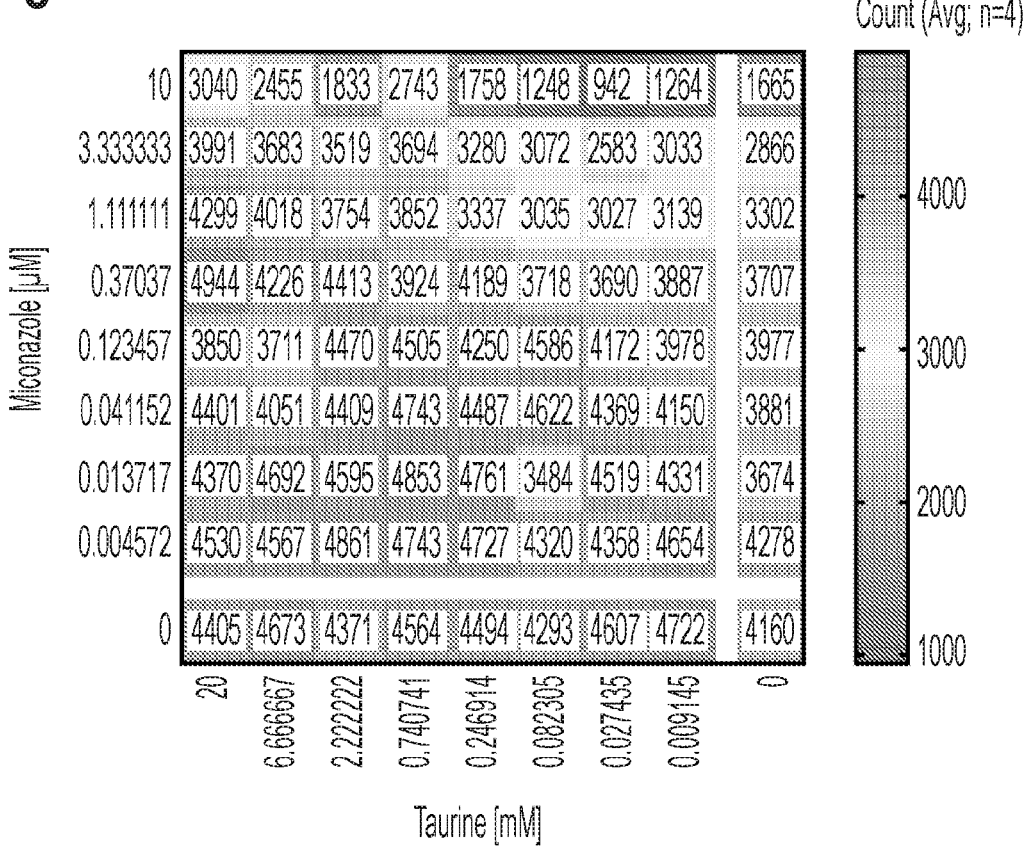

Fig. 9
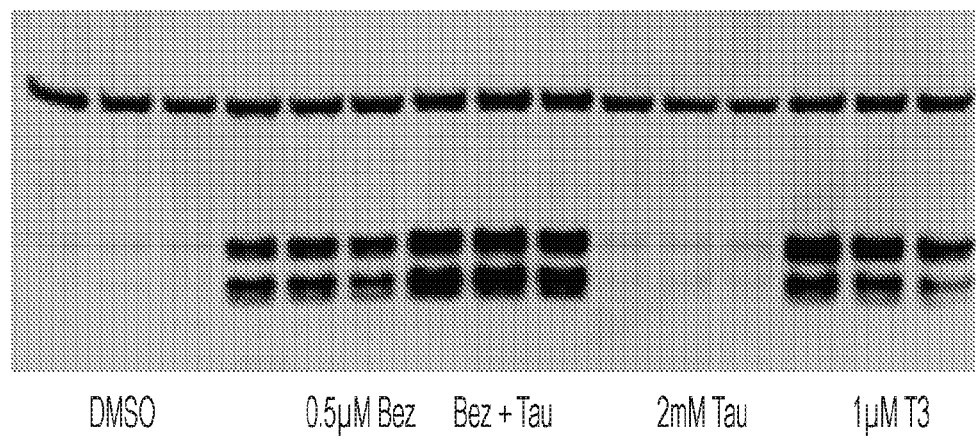
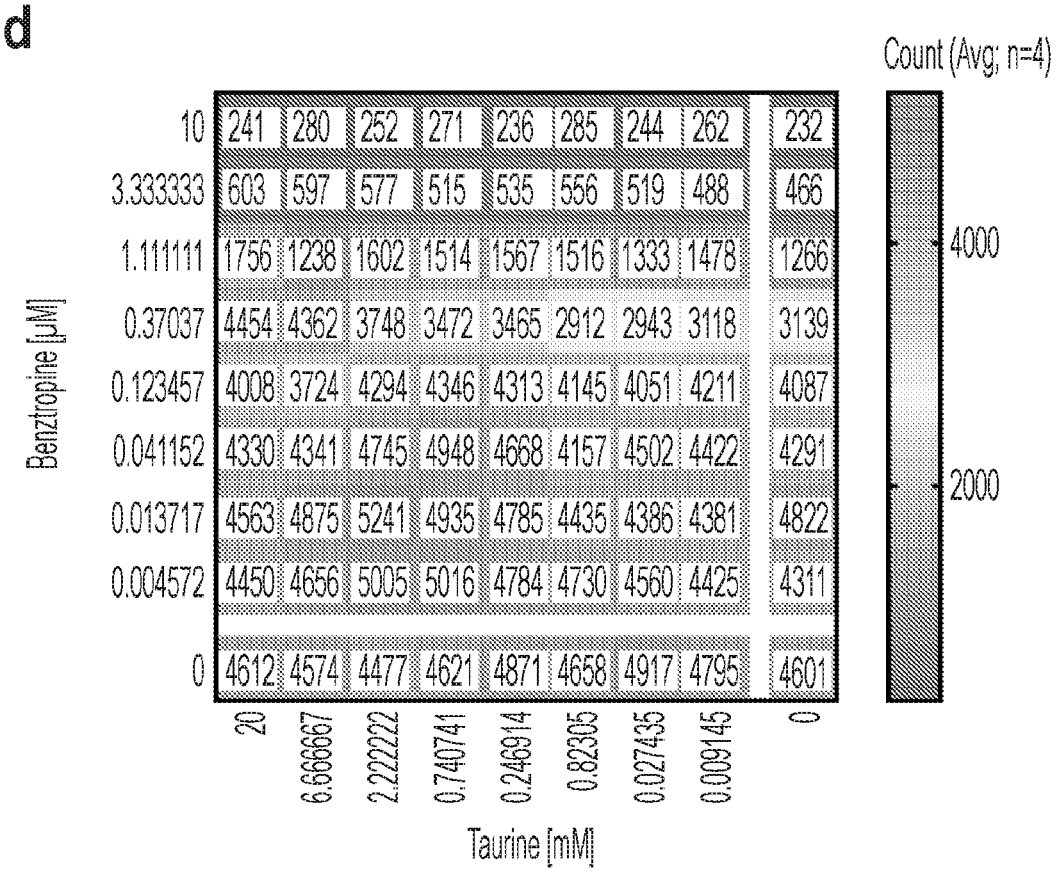

Fig. 10
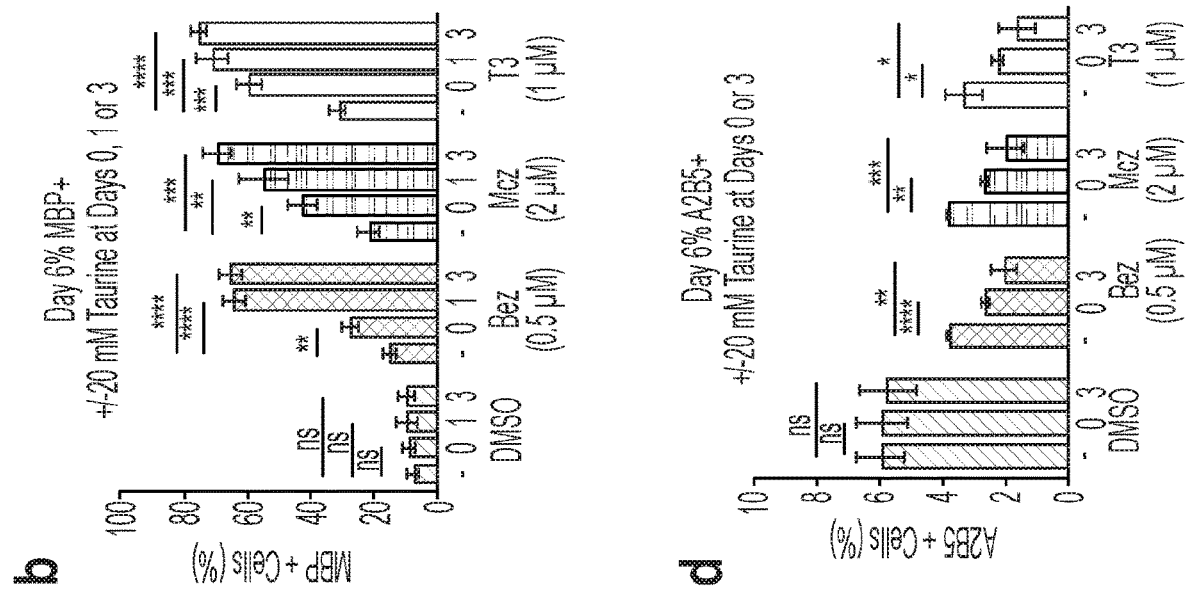
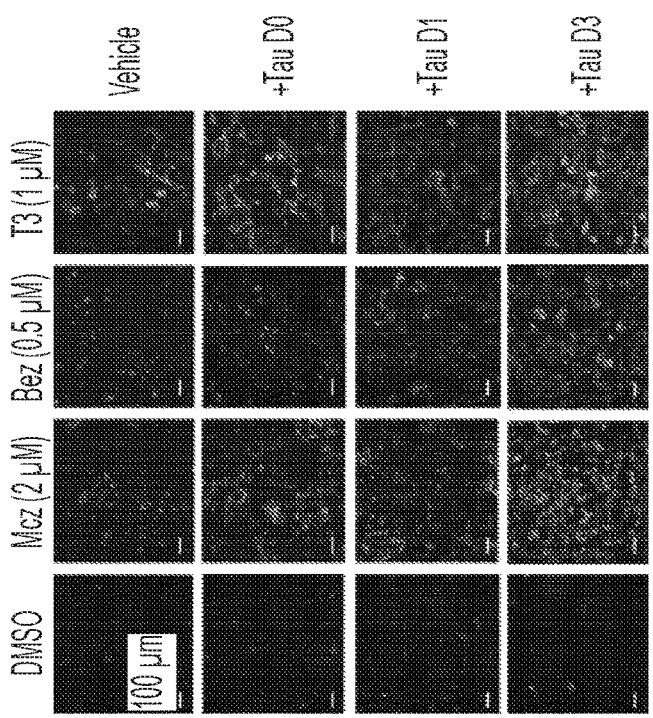

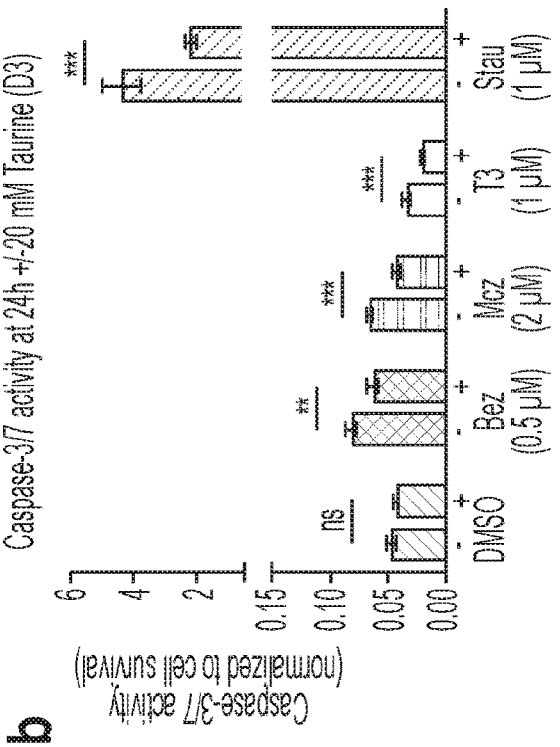
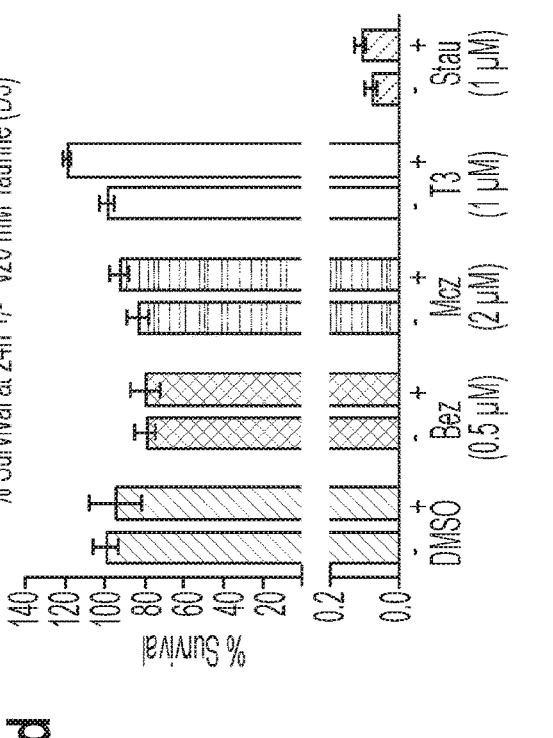
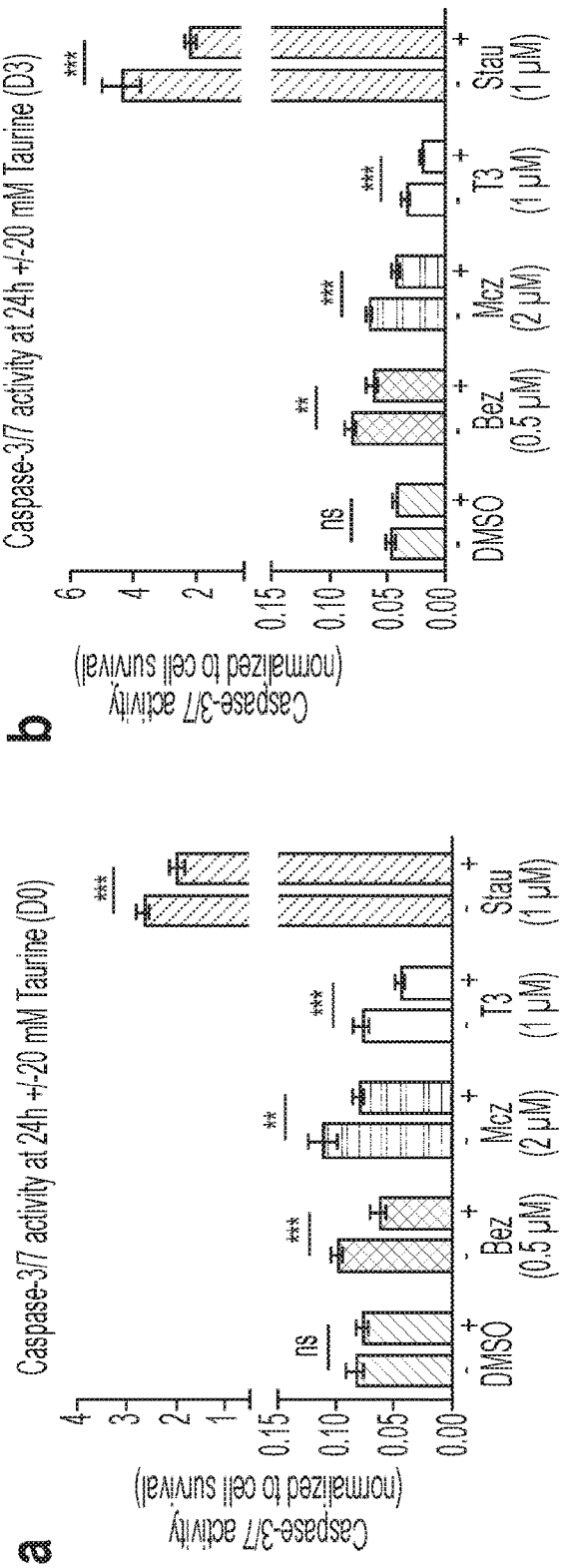
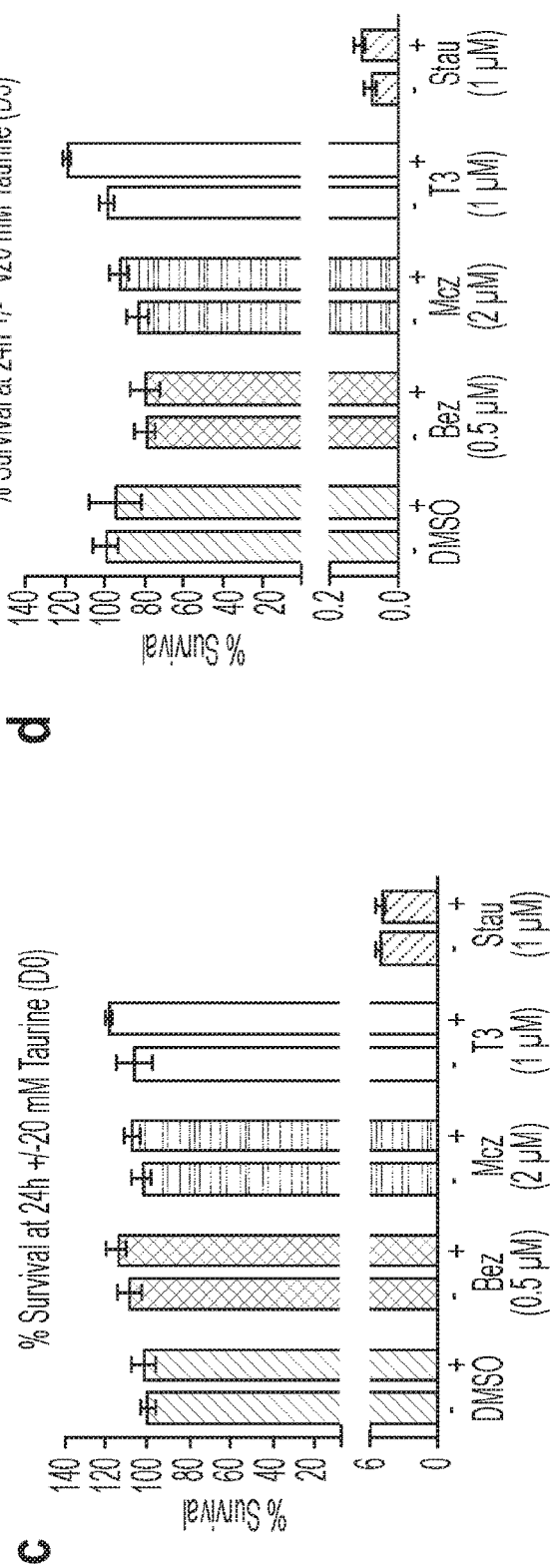
Fig. 11

METHODS FOR PROMOTING MYELINATION AND FOR TREATING DEMYELINATING DISEASES

CROSS-REFERENCE TO RELATED APPLICATIONS

The subject patent application claims the benefit of priority to U.S. Provisional Patent Application No. 62/640,151 (filed Mar. 8, 2018; now pending). The full disclosure of the priority application is incorporated herein by reference in its entirety and for all purposes.

STATEMENT OF GOVERNMENT SUPPORT

This invention was made with government support under grant numbers GM114368, EY017540, MH062261, DA026146, and OD016357 awarded by the National Institutes of Health, and grant numbers DE-FG02-07ER64325, DE-AC02-05CH11231 awarded by the United States Department of Energy. The government has certain rights in the invention.

BACKGROUND OF THE INVENTION

Multiple sclerosis (MS) is a debilitating demyelinating disease characterized by the primary demyelination of axons and subsequent neuronal dysfunction. Disease remission in MS is dependent on a regenerative process known as remyelination, which persists throughout adulthood and involves the migration and subsequent differentiation of oligodendrocyte precursor cells (OPCs), leading to the formation of newly formed oligodendrocytes. OPCs are found to be abundantly present in chronic lesions of MS patients and, as such, local inhibition of OPC differentiation is thought to be causative in MS disease progression. A promising complementary approach for the treatment of MS, as well as other demyelinating diseases, therefore, involves the identification of pharmacological agents that directly stimulate the process of remyelination by enhancing the process of OPC differentiation.

There is a need in the art for more effective therapies for treating demyelinating diseases such as MS. The present invention is directed to this and other unfulfilled needs in the art.

SUMMARY OF THE INVENTION

In one aspect, the present invention provides methods for treating or ameliorating symptoms of a demyelinating disease in a subject. The methods entail administering to the subject a pharmaceutical composition comprising a therapeutically effective amount of taurine or a taurine-like compound. Preferably, the compound is administered to the subject along with an agent that induces differentiation of oligodendrocyte precursor cells (OPCs) into oligodendrocytes. Co-administration of the compounds can result in treatment or amelioration of the symptoms of the demyelinating disease in the subject. In various embodiments, the OPC differentiation-inducing compound can be a muscarinic receptor antagonist, a dopamine receptor antagonist, a histamine receptor antagonist, a beta adrenergic receptor modulator, or an opioid receptor modulator. In some specific embodiments, the employed OPC differentiation-inducing compound is triiodothyronine (T3), miconazole, clobetasol, benztropine or clemastine. The taurine-like compound that can be used in the invention typically can upregulate serine levels to enhance glycosphingolipid biosynthesis in OPCs, pre-myelinating oligodendrocytes or oligodendrocytes. In various embodiments, the employed taurine-like compound is a taurine precursor, a taurine metabolite, a taurine derivative, a taurine analog or a substance required for taurine biosynthesis.

Some methods of the invention are directed to treating subjects afflicted with or at risk of developing multiple sclerosis (MS). In some preferred methods, the subject to be treated is a human. In some embodiments, the subject is additionally further treated with one or more known agents for treating demyelinating diseases or a known disease modifying drug, e.g., a S1P receptor agonist. In various embodiments, the S1PR agonist that can be employed in the methods of the invention is FTY720, MT1303, ACT-128800, BAF312, GSK2018682, CYM-5442, ONO-4641, AUY954, RG3477, SEW-2871, CS-0777, Syl930, AAL-R, RPC1063, RP-001, KRP-203, or CYM-5442. In methods utilizing a combination therapy, the known agent for treating demyelinating diseases can be administered to the subject prior to, simultaneously with, or subsequent to treatment with the taurine-containing pharmaceutical composition and/or the OPC differentiation-inducing compound. In some embodiments, the OPC differentiation inducing agent can also be included in the taurine-containing pharmaceutical composition.

In a related aspect, the invention provides methods for increasing myelination in a subject. The methods entail administering to the subject (a) a pharmaceutical composition comprising a therapeutically effective amount of taurine or a taurine-like compound and (b) an agent that induces OPC differentiation. In various embodiments, the employed OPC differentiation-inducing compound can be a muscarinic receptor antagonist, a dopamine receptor antagonist, a histamine receptor antagonist, a beta adrenergic receptor modulator, or an opioid receptor modulator. In some embodiments, the employed OPC differentiation-inducing agent is triiodothyronine (T3), miconazole, clobetasol, benztropine or clemastine. The taurine-like compound that can be used in these methods typically can upregulate serine levels to enhance glycosphingolipid biosynthesis in OPCs, pre-myelinating oligodendrocytes or oligodendrocytes. In various embodiments, the employed taurine-like compound is a taurine precursor, a taurine metabolite, a taurine derivative, a taurine analog or a substance required for taurine biosynthesis. Some of the methods are directed to human subjects. In some different embodiments, the pharmaceutical composition is administered to the subject simultaneously with, prior to, or subsequent to administration of the OPC differentiation-inducing agent. Some methods of the invention are directed to promoting myelination in the central nervous system of subjects who are afflicted with or at risk of developing a demyelinating disease. For example, subjects suffering from multiple sclerosis (MS) can be readily treated with the methods of the invention for promoting myelination in the CNS. In some embodiments, the subject can be additionally treated with a known agent for treating demyelinating diseases. In some of these embodiments, the employed agent for treating demyelinating diseases can be a S1P receptor agonist.

In a related aspect, the invention provides methods for promoting oligodendrocyte precursor cell (OPC) differentiation into oligodendrocytes. These methods entail contacting a population of OPCs with (a) a therapeutically effective amount of taurine or a taurine-like compound and (b) an agent that induces OPC differentiation. In some different embodiments, the OPC differentiation-inducing agent used in the methods can be triiodothyronine (T3), miconazole, clobetasol, benztropine or clemastine. In some embodiments, the methods of promoting OPC differentiation are performed in vitro, e.g., with a cultured population of OPCs. In some other embodiments, the methods can be performed in vivo in a subject. Some of these methods are directed to promoting OPC differentiation in a subject that is afflicted with or at risk of developing a demyelinating disease such as MS.

In another aspect, the invention provides pharmaceutical compositions or therapeutic kits for use in the various therapeutic methods described herein, e.g., for treating or ameliorating symptoms of a demyelinating disease. Typically, the pharmaceutical compositions or therapeutic kits contain a therapeutically effective amount of taurine or a taurine-like compound, and a pharmaceutically acceptable carrier. In some embodiments, the compositions or kits can additionally contain one or more agents for inducing OPC differentiation and/or a known agent for treating demyelinating diseases.

A further understanding of the nature and advantages of the present invention may be realized by reference to the remaining portions of the specification and claims.

DESCRIPTION OF THE DRAWINGS

FIG. 1 shows metabolic differences observed between T3- and DMSO-treated OPCs. (a) Fold change of 22 upregulated metabolites (excluding lipids) in OPCs treated for 6 days with T3 (1 µM), compared to DMSO treatment, determined using accurate mass and MS/MS data and significant pathway enrichment analyzed by Metaboanalyst (http://www.metaboanalyst.ca/) ($p<0.05$; n=5 replicate cell cultures). "MET" is the abbreviation of "metabolic pathway". (b) Targeted analysis of creatine and taurine pathways metabolites using triple-quad mass spectrometry (QQQ-MS) in multiple reaction monitoring (MRM) mode (n=5 replicate cell cultures). The numbers represent fold change by comparing T3 and DMSO treated OPCs. Values smaller than one suggest down-regulation while values larger than one (darker outline) suggest up-regulation in T3 treated OPC. White indicates non-detected (<LOD).

FIG. 2 shows impact of taurine treatment on the efficacy of drug-induced OPC differentiation. (a) MBP expression following 6 days of differentiation with miconazole (2 µM), miconazole (2 µM) plus taurine (2 mM) or taurine (2 mM) alone. Miconazole treatment initiated at day 0 and taurine treatment initiated at day 2. The data are mean±SD (n=3 replicate cell cultures) and normalized to MBP levels observed following induction with T3 (1 µM). Dotted line represents DMSO activity. β-actin used as internal control. Full gel provided in FIG. 9a. (b) MBP expression following 6 days of differentiation with benztropine (0.5 µM), benztropine (0.5 µM) plus taurine (2 mM) or taurine (2 mM) alone. Benztropine treatment initiated at day 0 and taurine treatment initiated at day 2. The data are mean±SD (n=3 replicate cell cultures) and normalized to MBP levels observed following induction with T3 (1 µM). Dotted line represents DMSO activity. β-actin used as internal control. Full gel provided in FIG. 9b. (c) and (d) High content imaging analysis, based on MBP immunofluorescent analysis (MBP, green; DAPI, blue), of DMSO, taurine (20 mM), miconazole (3 µM), miconazole (3 µM) plus taurine (20 mM), benztropine (3 µM), and benztropine (3 µM) plus taurine (20 mM). Data are mean±SD for the percentage of MBP-positive cells per well (n=4 replicate cell cultures). "Bez", "Mcz" and "Tau" are the abbreviations for "benztropine", "miconazole" and "taurine"; respectively. "ns", "*", "", and "**" represent no significance, $p<0.05$, $p<0.01$, and $p<0.0001$; respectively.

"ns", "*", "", and "**" represent no significance, p<0.05, p<0.01, and p<0.0001; respectively.

Figure 6:
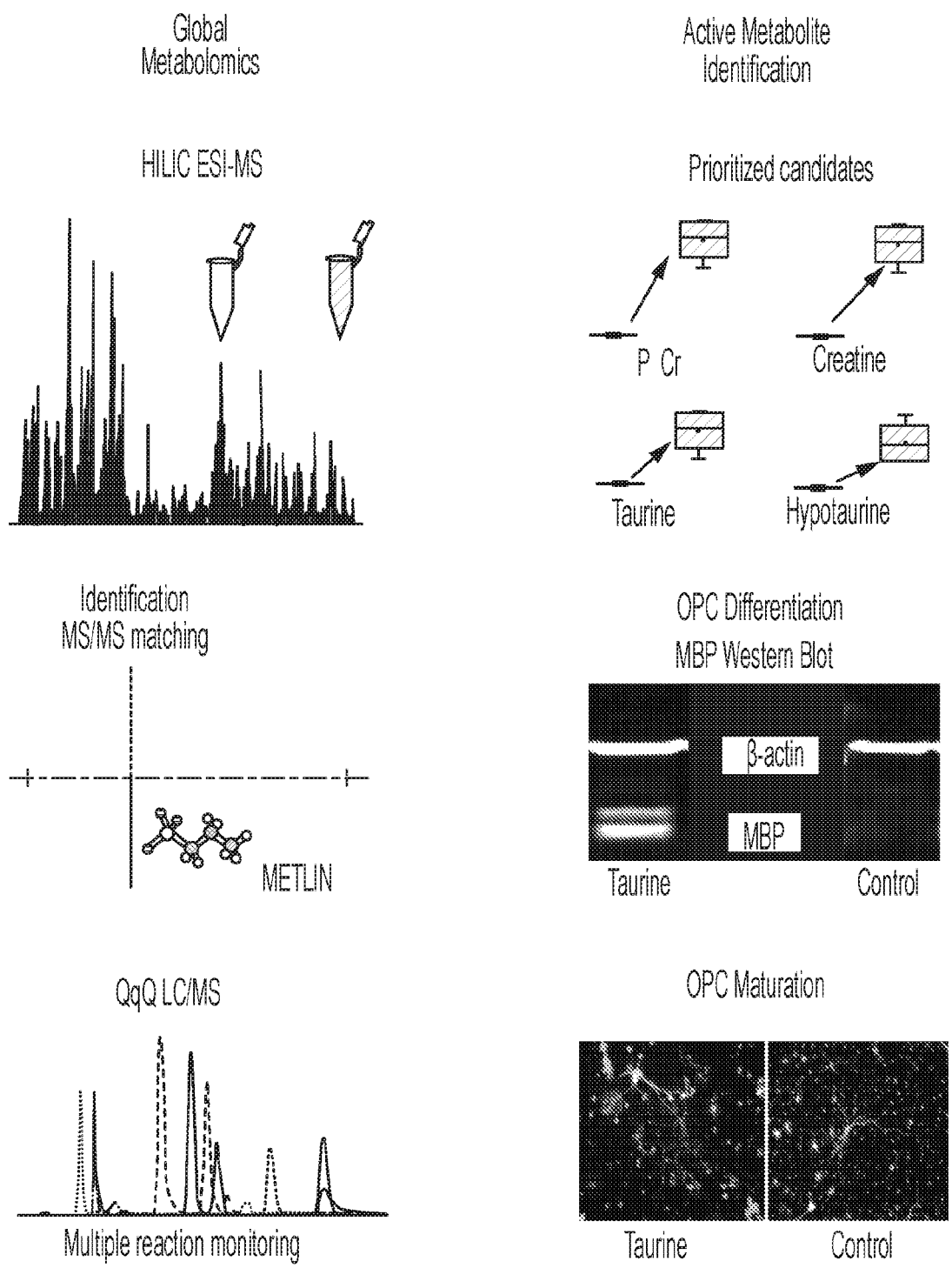

FIG. 6 shows experimental metabolomics discovery workflow. OPCs treated with DMSO and T3 for 6 days were extracted and analyzed using untargeted HILIC/MS profiling in ESI negative mode. LC/MS data acquisition was followed by retention time correction and chromatogram alignment using online XCMS. Metabolite features whose levels significantly changed (fold change>1.5 and p<0.01) were filtered out and identified by MS/MS matching. The identified metabolites, as well as other key up or downstream metabolites, which were not identified by global metabolomics analysis, were quantified by more sensitive targeted MRM analysis using authentic compound standards. A list of endogenous metabolites was prioritized for evaluation in the in vitro OPC differentiation assay. Impact on differentiation was determined based on MBP expression. In vitro OL maturation was evaluated using a co-culture assay involving primary mouse cortical neurons and OPCs.

FIG. 7 shows comparative lipidomics profiling of OPCs treated with DMSO or T3 (1 µM) for 6 days. (a) Cloud plot showing dysregulated features between OPCs treated with DMSO and T3 at Day 6. Features were filtered using p<0.01, intensity >10,000 and fold change >1.5 (n=5 replicate cell cultures). (b) Principal component analysis scores plots. (c) Degree of unsaturation in OPCs. The plot shows the relative fold change of metabolites that are upregulated in OPCs and ODs. (d) The proportion distribution of lipids upregulated in OPCs and ODs with different unsaturation degrees (0-1, 1-3, and 3-14).

Figure 8:
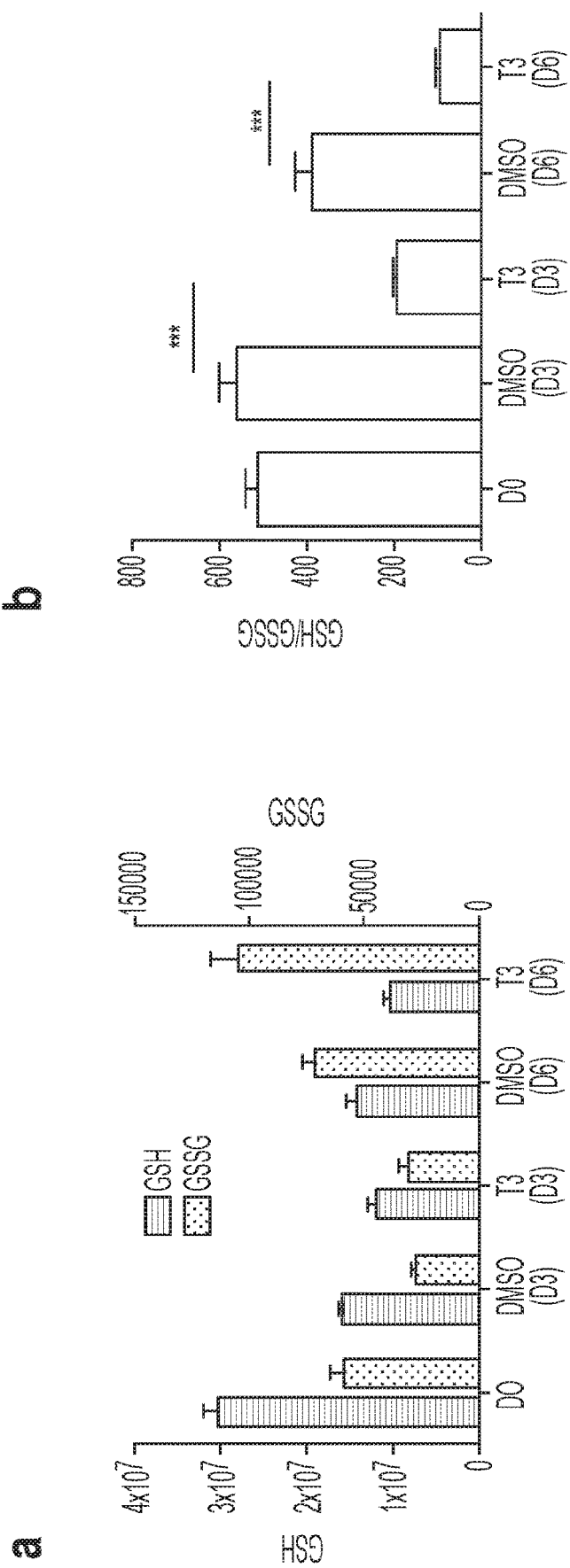

FIG. 8 shows glutathione (GSH), oxidized glutathione (GSSG), and their GSH/GSSG ratio at Day 0, 3 or 6 for OPC cultures treated with DMSO or T3 (1 µM). Data are mean±SD (n=3 replicate cell cultures for each condition). "***" represents p<0.001.

FIG. 9 shows impact of taurine treatment on OPC differentiation. (a) MBP expression following 6 days of differentiation with miconazole (2 µM), miconazole (2 µM) plus taurine (2 mM) or taurine (2 mM) alone. Miconazole treatment initiated at day 0 and taurine treatment initiated at day 2 (n=3 replicate cell cultures). (b) MBP expression following 6 days of differentiation with benztropine (0.5 µM), benztropine (0.5 µM) plus taurine (2 mM) or taurine (2 mM) alone. Benztropine treatment initiated at day 0 and taurine treatment initiated at day 2 (n=3 replicate cell cultures). "Bez", "Mcz" and "Tau" are the abbreviations for "benztropine", "miconazole" and "taurine"; respectively. (c and d) Imaging-based cell counting (n=4 replicate cell cultures for each condition) of (c) Miconazole+taurine and (d) Benztropine+taurine-treated OPCs with variable combinations of concentration.

FIG. 10 shows temporal effects of taurine addition on efficacy of drug-induced OPC differentiation. Results shown were based on time course images of MBP-positive oligodendrocytes on day 6 post-treatment with DMSO, Miconazole (2 µM), Benztropine (0.5 µM), or T3 (1 µM), with or without taurine (20 mM) addition on days 0-3. (a) Quantification of MBP-positive OLs from the time course study, based on automated image analysis. (b) and (c) Impact of taurine addition on A2B5-positive immature OPC numbers at various stages of oligodendrocyte differentiation. Percentage of A2B5+ nuclei quantified on Day 3 following addition of 20 mM taurine on days 0 or 1 (c) and quantified on Day 6 following addition of 20 mM taurine on days 0 or 3. Benztropine (0.5 µM), miconazole (2 µM), and T3 (1 µM) were each added on day 0. Data are mean±SD for the percentage of MBP-positive cells per well (n=3 replicate cell cultures). "Bez", "Mcz" and "Tau" are the abbreviations for "benztropine", "miconazole" and "taurine"; respectively. "ns", "*", "", "*", and "****" represent no significance, p<0.05, p<0.01, p<0.001 and p<0.0001; respectively.

FIG. 11 shows comparative effects of taurine treatment on apoptosis in OPCs and premyelinating OLs. Activity of the apoptosis indicator Caspase-3/7 is shown 24 h after addition of 20 mM taurine on (a) Day 0 (D0) or (b) Day 3 (D3). Benztropine (0.5 µM), miconazole (2 µM), and T3 (1 µM) were each added on day 0. (c) and (d) Parallel quantitative analysis of cell survival for treatments described in (a) and (b). "Bez", "Mcz" and "Stau" are the abbreviations for "benztropine", "miconazole" and "staurosporine"; respectively. Data are mean±SD (n=3 replicate cell cultures). "ns", "", and "*" represent no significance, p<0.01, and p<0.001; respectively.

Figure 12:
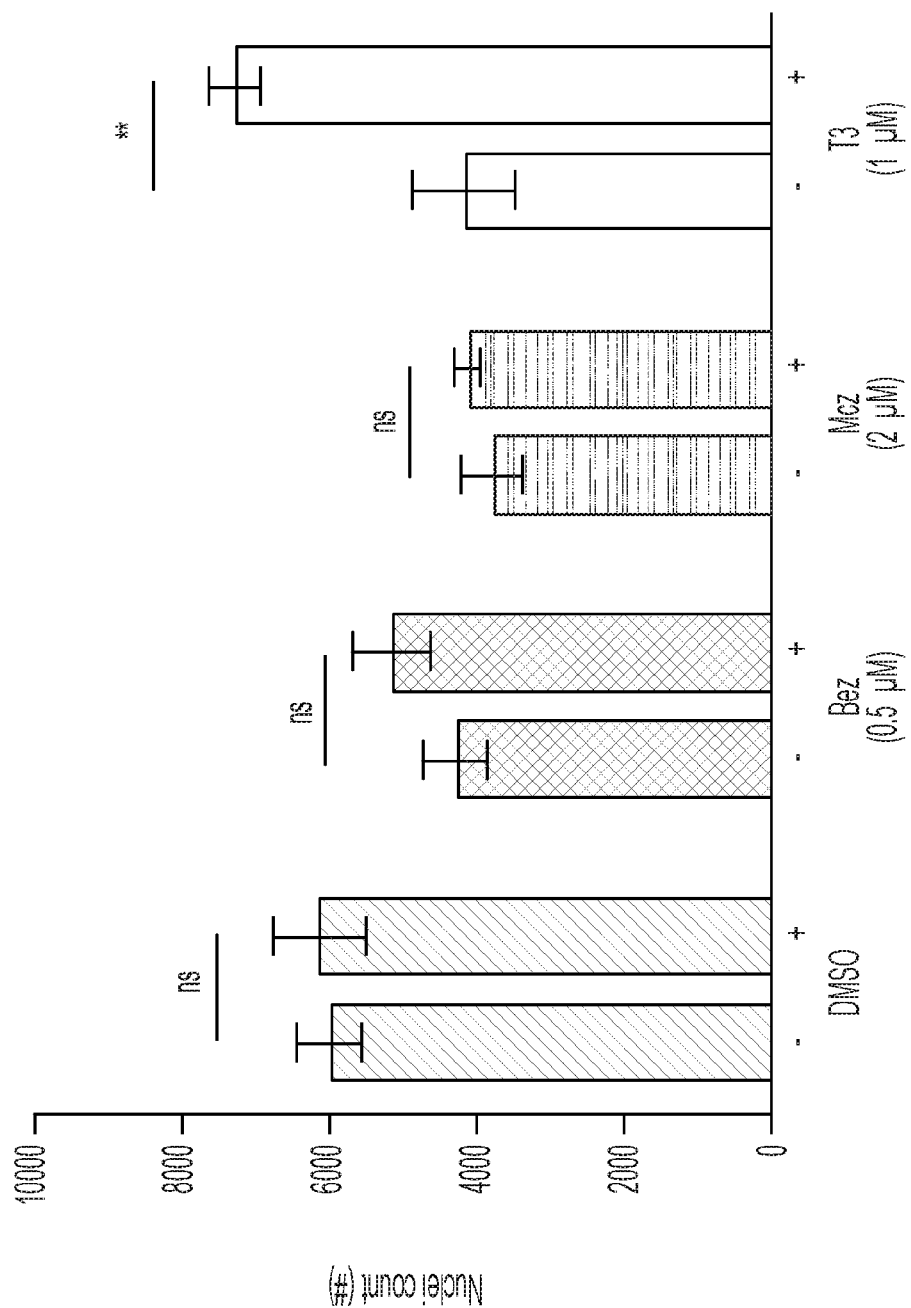

FIG. 12 shows impact of alternative reducing agents on drug-induced OPC differentiation. Results shown were obtained from images of MBP expression following 6 days of treatment with Benztropine (0.5 µM), miconazole (2 µM) or T3 (1 µM) in the presence or absence of reduced glutathione. The data are based on parallel quantitative imaging-based analysis of cell survival for treatments. Data are mean±SD (n=3 replicate cell cultures). "Bez" and "Mcz" are the abbreviations for "benztropine" and "miconazole"; respectively. "ns" and "**" represent no significance and p<0.01; respectively.

Figure 13:
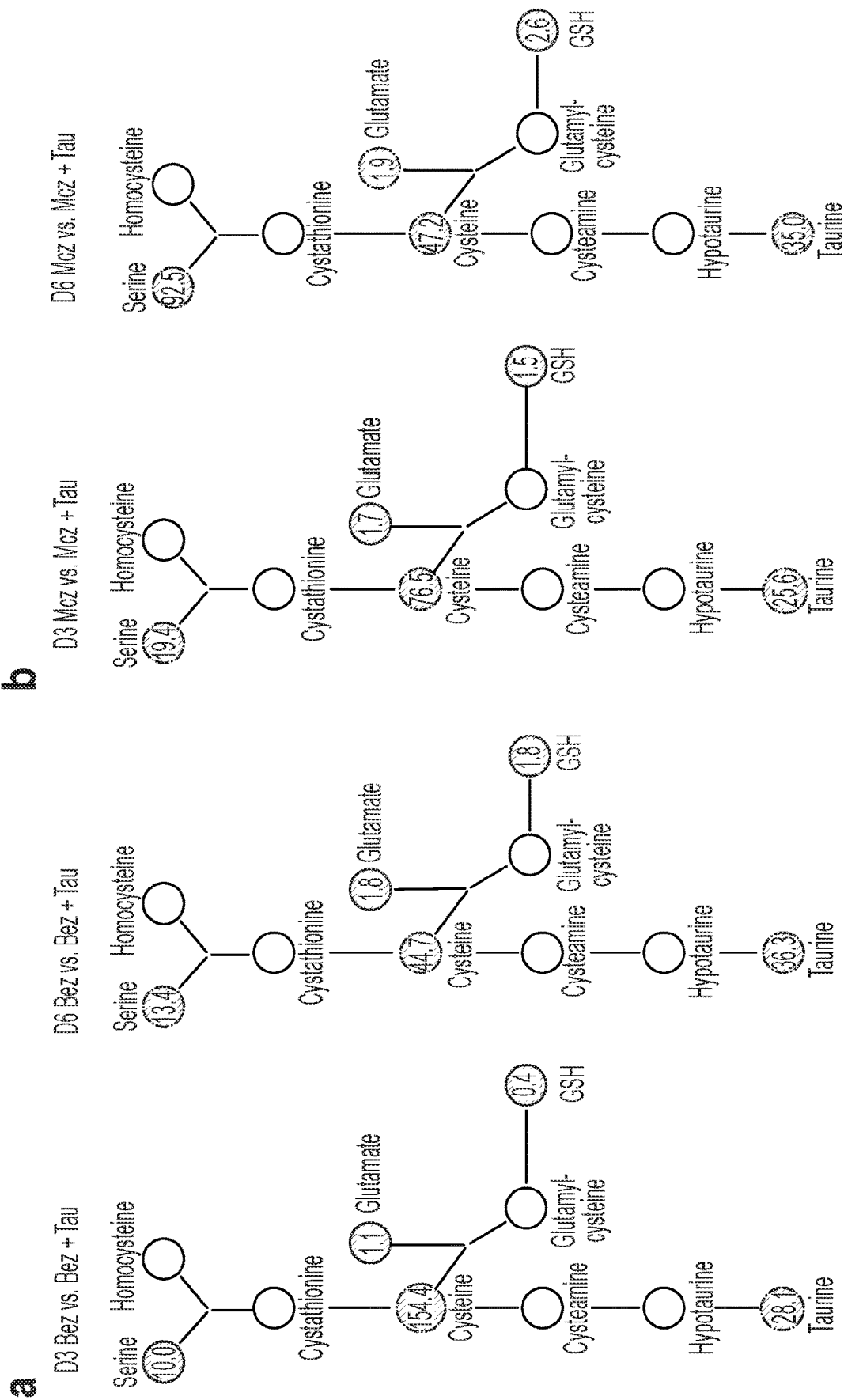

FIG. 13 shows binary global metabolomics analysis of taurine co-treatment. (a) Binary global metabolomics analysis of the impact of taurine (20 mM) supplementation on pre-myelinating OLs (harvested on day 3, D3) and OLs (harvested on day 6, D6) differentiated using Benztropine (0.5 µM) (a) or Miconazole (2 µM). Drug and taurine treatment initiated on day 0 (b). Numbers represent fold changes of metabolites, with values smaller than one suggesting down-regulation and values larger than one suggesting up-regulation. White indicates non-detected (i.e., below limit of detection). Darker circles represent a p-value <0.05.

Figure 14:
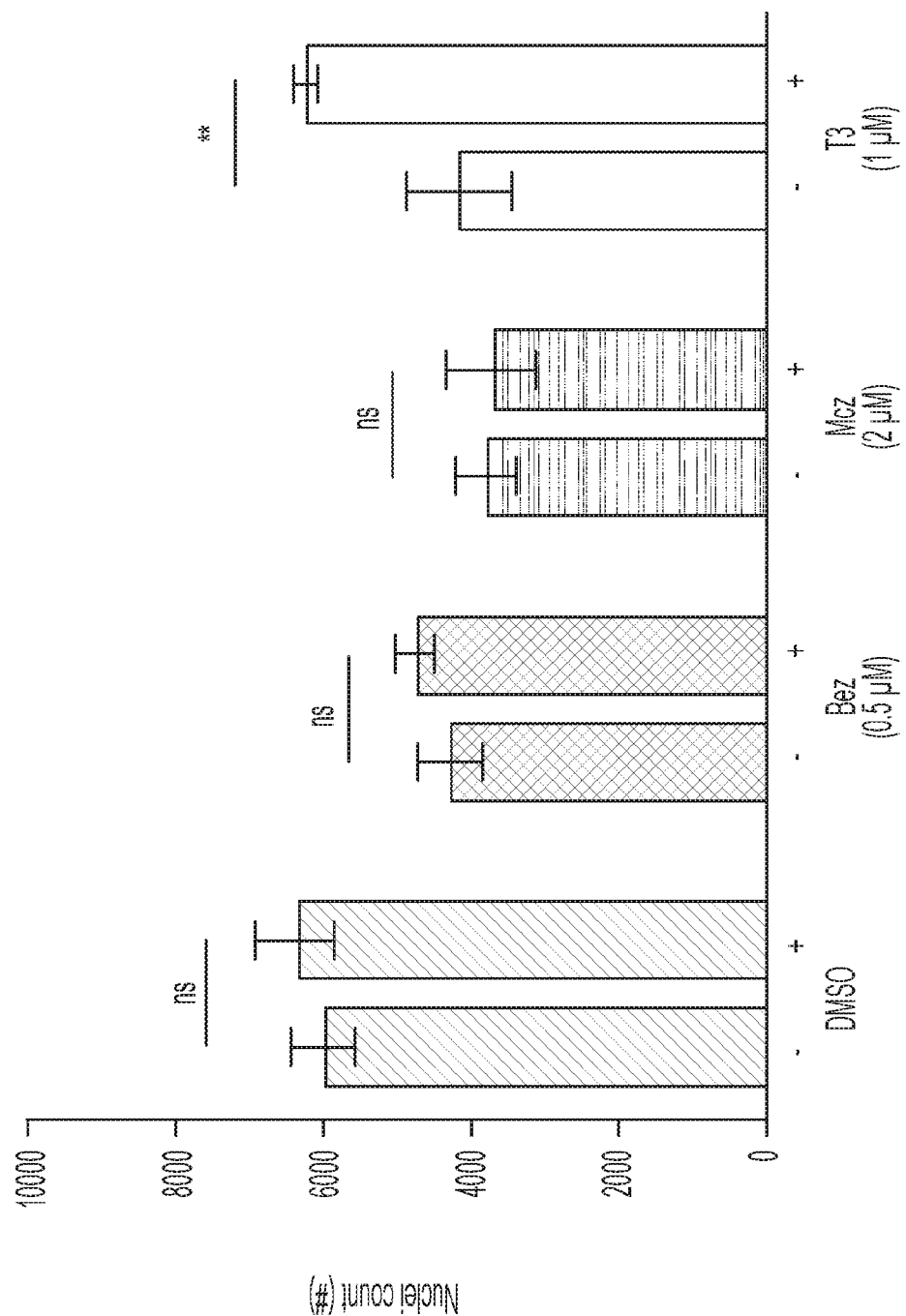

FIG. 14 shows impact of propargyl glycine (PPG) on drug-induced OPC differentiation. Results shown in the figure were obtained from images of MBP expression following 6 days of treatment with Benztropine (0.5 µM), miconazole (2 µM), and T3 (1 µM) in the absence or presence of PPG (10 µM). Drug and PPG treatment initiated on day 0. Note, for comparison, images for vehicle treatment are identical to those used in FIG. 12. The data are based on parallel quantitative imaging-based analysis of cell survival for treatments. Data are mean±SD (n=3 replicate cell cultures). "Bez" and "Mcz" are the abbreviations for "benztropine" and "miconazole"; respectively. "ns" and "**" represent no significance, and p<0.01; respectively.

Figure 15:
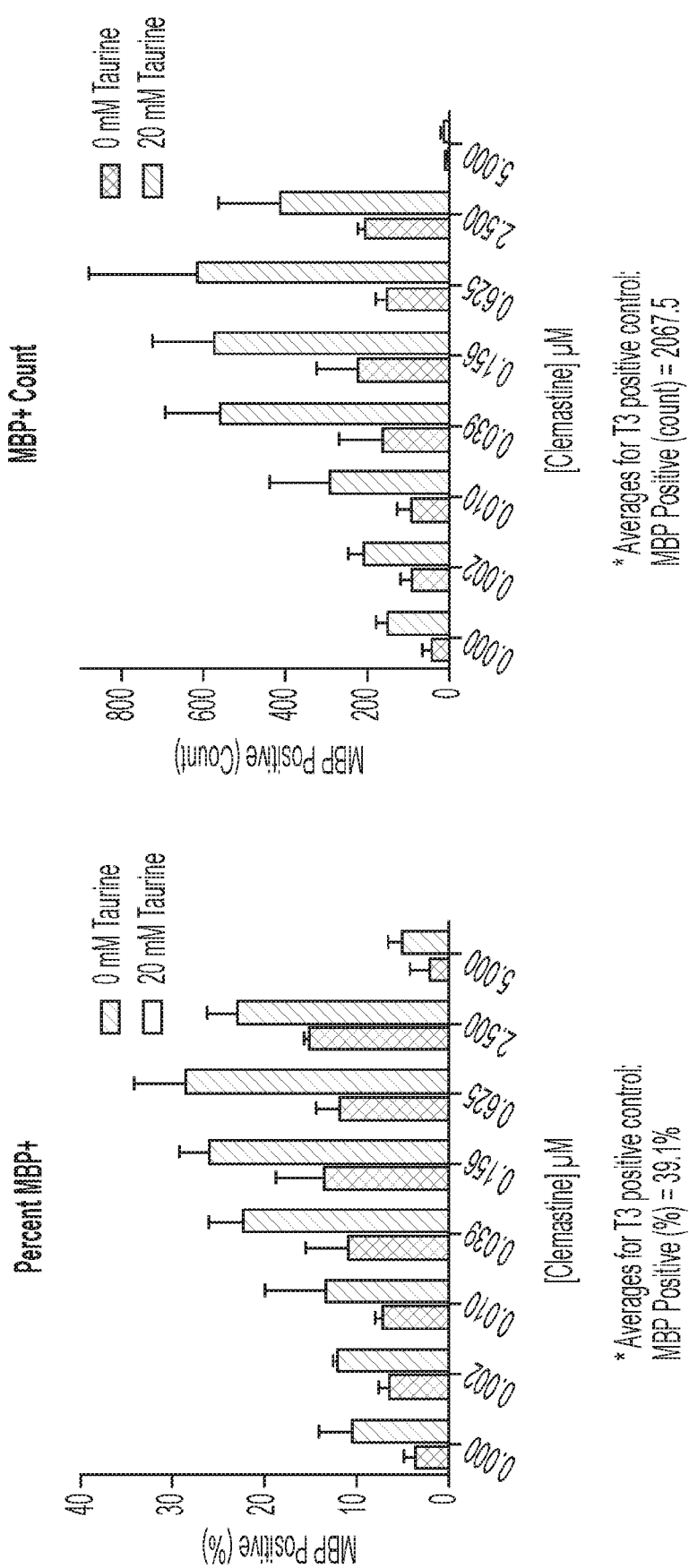

FIG. 15 shows impact of taurine on clemastine-induced oligodendrocyte maturation. The experimental design, analysis and interpretation are the same as that for studies on taurine impact on oligodendrocyte maturation induced by benztropine, miconazole and T3.

DETAILED DESCRIPTION

Endogenous metabolites play essential roles in the regulation of cellular identity and activity. The present invention is predicated in part on the discovery by the present inventors that an endogenous metabolite enhances the maturation of oligodendrocytes. With the goal of identifying mechanisms and molecules that could be used in the development of new treatment strategies for MS, the inventors used a global metabolomics approach to successfully identify endogenous metabolites that are significantly altered over the course of the OPC differentiation process and can serve to directly impact cell fate. Specifically, the inventors investigated the process of oligodendrocyte precursor cell (OPC) differentiation, a process which becomes limiting during progressive stages of demyelinating diseases, including multiple sclerosis (MS), using mass spectrometry-based global metabolomics approach. Levels of taurine, an amino sulfonic acid possessing pleotropic biological activities and broad tissue distribution properties, were found to be significantly elevated (~20-fold) during the course of oligodendrocyte differentiation and maturation. When added exogenously at physiologically relevant concentrations, taurine was found to dramatically enhance the processes of drug-induced in vitro OPC differentiation and maturation. Mechanism of action studies suggest that the oligodendrocyte differentiation-enhancing activities of taurine are driven primarily by its ability to directly increase available serine pools, which serves as the initial building block required for the synthesis of the glycosphingolipid components of myelin that define the functional oligodendrocyte cell state.

In accordance with these discoveries, the present invention provides novel methods of using taurine for increasing myelination in the central nervous system and for treating or ameliorating symptoms of demyelinating diseases such as MS. In accordance with the invention, subjects who are afflicted with a demyelinating disease, who are suspected of having a demyelinating disease, and who are at risk of developing a demyelinating disease can be treated therapeutically or prophylactically with taurine. Preferably, the subject is administered with taurine in combination with a compound that induces differentiation of OPC into oligodendrocytes. Further, these subjects can be treated with these compounds in conjunction with other known therapies for those diseases. For example, some methods of the invention are directed to treating subjects with a combination of taurine, an OPC differentiation-inducing agent (e.g., T3, benztropine or miconazole), and a SW receptor agonist or a known disease-modifying drug.

In addition to methods of treating demyelinating diseases and methods of increasing myelination, the invention also provides methods of using taurine and OPC differentiation-inducing drugs to promote OPC differentiation into oligodendrocytes. As described herein, such methods can be performed by contacting OPC with the compounds in vitro or ex vivo. The methods can also be performed in vivo, e.g., by administering the compounds to a subject who is afflicted with at risk of developing a demyelinating disease such as MS.

The following disclosures provide more detailed guidance for making and using the compositions of the invention, and for carrying out the methods of the invention.

Unless otherwise indicated, the invention can employ conventional techniques of cell biology, cell culture, molecular biology, transgenic biology, microbiology, recombinant DNA, and immunology, which are within the skill of the art. Such techniques are explained fully in the literature. See, for example, Sambrook et al, ed. (1989) Molecular Cloning A Laboratory Manual (2nd ed.; Cold Spring Harbor Laboratory Press); Sambrook et al, ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al, eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press ($1^{st}$ ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons ($3^{rd}$ ed., 2002); *Dictionary of Chemistry*, Hunt (Ed.), Routledge ($1^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (*Oxford Paperback Reference*), Martin and Hine (Eds.), Oxford University Press ($4^{th}$ ed., 2000). In addition, the following definitions are provided to assist the reader in the practice of the invention.

The term "agent" or "test agent" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" can be used interchangeably.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved traits (such as higher binding affinity for a target molecule) is an approach that is well known in pharmaceutical chemistry.

Demyelinating diseases refer to any condition that results in damage to the protective covering (myelin sheath) that surrounds nerve fibers in your brain, optic nerves and spinal cord. See, e.g., Pouly et al., *J Autoimmun* 13, 297-306 (1999) and Franklin et al., *Nat Rev Neurosci* 9, 839-855 (2008). When the myelin sheath is damaged, nerve impulses slow or even stop, causing neurological problems. Multiple sclerosis (MS) is the most common demyelinating disease of the central nervous system. In this disorder, the immune system attacks the myelin sheath or the cells that produce and maintain it. This causes inflammation and injury to the sheath and ultimately to the nerve fibers that it surrounds.

The process can result in multiple areas of scarring (sclerosis). Other examples of demyelinating disease and their causes include, e.g., optic neuritis—inflammation of the optic nerve in one or both eyes; neuromyelitis optica (Devic's disease)—inflammation and demyelination of the central nervous system, especially of the optic nerve and spinal cord; Transverse myelitis—inflammation of the spinal cord; acute disseminated encephalomyelitis—inflammation of the brain and spinal cord; and adrenoleukodystrophy and adrenomyeloneuropathy—rare, inherited metabolic disorders.

As used herein, the term "subject suspected of having demyelinating disease" refers to a subject that presents one or more symptoms indicative of a demyelinating disease (e.g., MS) or is being screened for the disease (e.g., during a routine physical). A subject suspected of having a demyelinating disease may also have one or more risk factors. A subject suspected of having a demyelinating disease has generally not been tested for demyelinating disease. However, a "subject suspected of having demyelinating disease" encompasses an individual who has received an initial diagnosis but for whom the severity of the demyelinating disease is not known. The term further includes people who once had a demyelinating disease but whose symptoms have ameliorated. In contrast, a "subject identified as having a demyelinating disease" refers to a subject that have been diagnosed by a physician (e.g., using methods well known in the art) as having a demyelinating disease.

As used herein, the term "subject at risk of developing demyelinating disease" refers to a subject with one or more risk factors for developing a demyelinating disease. Risk factors include, but are not limited to, gender, age, genetic predisposition, environmental exposure, previous incidents of demyelinating disease, preexisting non-demyelinating diseases, and lifestyle.

S1P receptors are known to be involved in regulation of a number of physiological processes, such as vascular cell systems, vascular permeability, cardiac cell systems, and lymphocyte trafficking. Diseases associated with receptors refer to medical disorders or conditions which are mediated by one or more of the S1P receptors (e.g., S1P1), or in which signaling by one or more of the S1P receptors play an important and contributory role. These include autoimmune diseases, transplant rejections, atherosclerosis, and etc. Specific examples of such diseases are described herein.

An S1P1 selective agonist compound is a compound which selectively binds to and/or activates S1P1, but not one or more of the other S1P receptors (e.g., S1P2, S1P4 and S1P5). Typically, it will have a much higher binding affinity for S1P1 and S1P3 and a much higher potency in inducing S1P1-mediated activities than that for one or more of the other S1P-specific receptors. For example, if measured in a GTP-γS binding assay, an S1P1 selective compound typically has an EC50 (effective concentration that causes 50% of the maximum response) for S1PR1 in the range of $1 \times 10^{-10}$ to $1 \times 10^{-5}$ M, preferably less than 50 nM, more preferably less than 5 nM. Additionally or alternatively, the S1P1 selective compound can have an EC50 for one or more of the other S1P-specific receptors that is at least 5, 10, 25, 50, 100, 500, or 1000 fold higher than its EC50 for S1PR1, as measured in, e.g., a GTP-γS binding assay. Thus, some of the S1P1 selective agonists will have an EC50 for S1PR1 that is less than 5 nM while their EC50s for one or more the other S1P receptors are at least 100 nM or higher.

The term "biological sample" refers to sections of tissues such as biopsy and autopsy samples, and frozen sections taken for histologic purposes. Such samples include blood (e.g., peripheral blood), sputum, tissue, cultured cells, e.g., primary cultures, explants, and transformed cells, stool, urine, etc. A biological sample is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish.

The term "contacting" has its normal meaning and refers to combining two or more agents (e.g., polypeptides or small molecule compounds) or combining agents and cells (e.g., a small molecule and a cell). Contacting can occur in vitro, e.g., combining two or more agents or combining a test agent and a cell or a cell lysate in a test tube or other container. Contacting can also occur in a cell or in situ, e.g., contacting two polypeptides in a cell by coexpression in the cell of recombinant polynucleotides encoding the two polypeptides, or in a cell lysate.

The term "modulation" or "modulating" refers to the activity of a compound or other agent in evoking a change in a biological activity of, or a functional response mediated by, another molecule. The term "modulate" refers to a change in the biological or cellular activities (e.g., expression or signaling activities) of the target molecule. Modulation can be up-regulation (i.e., activation or stimulation) or down-regulation (i.e. inhibition or suppression). For example, modulation may cause a change in ligand binding characteristics, or any other biological activities or functions of, or cellular or immunological activities mediated by, the target molecule. The mode of action can be direct, e.g., through binding to the target molecule. The change can also be indirect, e.g., through binding to and/or modifying (e.g., enzymatically) another molecule which otherwise modulates the target molecule.

Myelination refers to the process of forming a fatty coating called myelin over the axon of each neuron. Myelination protects the neuron and helps it conduct signals more efficiently.

The term "subject" refers to human and other primates such as monkeys, gorillas, dog, cat, pigs, rabbits, bovine, equine, ovine, other domestic animals, and etc.

As used herein, the term "taurine" refers to 2-aminoethanesulfonic acid. The term "taurine-like compounds" broadly include any compounds that can mimic taurine in directly or indirectly upregulating serine levels to enhance glycosphingolipid biosynthesis in OPCs, pre-myelinating oligodendrocytes or oligodendrocytes. These include compounds that, in addition to the functional similarity to taurine, are also structurally similar or substantially identical to taurine (e.g., derivatives). In various embodiments, they encompass taurine precursors, taurine metabolites, taurine derivatives, taurine analogs and substances required for the taurine biosynthesis. As used herein, "taurine precursors" encompass substances that, when they are administered to a human or an animal, can be transformed, directly or indirectly, into taurine. The term "taurine metabolites" encompass substances that are produced in vivo by transformation of taurine. The term "taurine derivatives" encompass substances that are structurally close to taurine but possess at least one structural difference, such as one or more chemical changes, e.g. at least one replacement of an atom or a chemical group found in taurine by a distinct atom or a distinct chemical group. The term "taurine analogs" encompass substances that are chemically distinct from taurine but which exert the same or similar biological activity noted above. The term "substances required for taurine biosynthesis" encompass all substances that are involved in the in vivo taurine biosynthesis including enzymes and enzyme cofactors, thus including cysteine dioxygenase (EC 1.13.11), sulfinoalanine decarboxylase (EC 4.1.1.29) and cofactors thereof.

A "variant" of a molecule refers to a molecule substantially similar in structure and biological activity to either the entire molecule, or to a fragment thereof. Thus, provided that two molecules possess a similar activity, they are considered variants as that term is used herein even if the composition or secondary, tertiary, or quaternary structure of one of the molecules is not identical to that found in the other, or if the sequence of amino acid residues is not identical.

The invention provides methods for treating or preventing demyelinating diseases such as multiple sclerosis (MS) in a subject. In some related embodiments, the invention provides methods for increasing myelination in the CNS of a subject. Preferably, the therapeutic methods of the invention involve administering to the subject taurine (or a taurine-like compound plus an OPC differentiation-inducing agent. In addition to taurine and the OPC differentiation-inducing agent, the subject can be additionally treated with a known agent for treating demyelinating diseases. For example, the treatment with taurine and the OPC differentiation-inducing agent can be combined with therapies for treating demyelinating diseases with S1P receptor agonists. In various embodiments, administration of these different agents to the subject can take place simultaneously or sequentially.

Subjects afflicted with, suspected of having, or at risk of developing any of the various demyelinating diseases can be treated with methods of the invention. Examples of demyelinating diseases that are suitable for treatment with methods of the invention include, e.g., acute disseminated encephalomyelitis (ADEM), acute hemorrhagic leukoencephalitis, acute optic neuritis, adrenoleukodystrophy, anti-MAG peripheral neuropathy, anti-MOG associated spectrum, Balo concentric sclerosis, brain injury, CAMFAK (cataracts, microcephaly, failure to thrive, and kyphoscoliosis) syndrome, Canavan disease, central pontine myelinolysis, Charcot-Marie-Tooth disease, chronic inflammatory demyelinating polyneuropathy, chronic relapsing inflammatory optic neuritis (CRION), clinically isolated syndrome (CIS), copper deficiency associated condition, diffuse cerebral sclerosis of Schilder (Schilder's disease), diffuse myelinoclastic sclerosis, Guillain-Barré syndrome, hereditary neuropathy, hereditary neuropathy with liability to pressure palsy, Krabbe disease, leukodystrophic disorders, Marburg multiple sclerosis, multiple sclerosis, myelinoclastic disorders, myelopathy, nerve injury, neuromyelitis optica, neuromyelitis optica (NMO), optic neuropathy, optic-spinal multiple sclerosis, Pelizaeus-Merzbacher disease, peripheral neuropathy, primary progressive multiple sclerosis (PPMS), progressive inflammatory neuropathy, progressive multifocal leukoencephalopathy, progressive-onset multiple sclerosis, relapsing-onset multiple sclerosis, relapsing-remitting multiple sclerosis (RRMS), secondary progressive multiple sclerosis (SPMS), Solitary sclerosis, Tabes dorsalis, and tumefactive multiple sclerosis.

Typically, the different compounds to be administered to the subject are provided in pharmaceutical composition. For example, administration of taurine involves a pharmaceutical composition that contains an effective amount of taurine or a taurine-like compound. In general, taurine-like compounds that can be used in the invention can be any compounds that can directly or indirectly upregulate serine level to enhance glycosphingolipid biosynthesis in OPCs, pre-myelinating oligodendrocytes or oligodendrocytes. In addition to such functional similarity to taurine, some taurine-like compounds can also be structurally similar to taurine. In various embodiments, they encompass taurine precursors, taurine metabolites, taurine derivatives, taurine analogs and substances required for the taurine biosynthesis. In some other embodiments, suitable compounds also include inhibitors of taurine biosynthesis pathway, e.g., propargyl glycine (PPG), which can block taurine biosynthesis but recapitulate the activity of taurine as exemplified herein.

Non-limiting examples of taurine precursors include cysteine, cystathionine, homocysteine, S-adenosylhomocysteine, serine, N-acetyl-cysteine, glutathione, N-formylmethionine, S-adenosylmethionine, betaine and methionine. Non-limiting examples of taurine metabolites include hypotaurine, thiotaurine, taurocholate, tauret also known as retinyliden taurine ((3,7-dimethyl-9-(2,6,6-trimethyl-1-cyclohexen-1-yl)-2,4,6,8-nonatetraen-1-imido-(N-ethane sulfonic acid)). Non-limiting examples of taurine derivatives include acetylhomotaurinate, and piperidino-, benzamido-, phthalimido- or phenylsuccinylimido taurine derivatives. Such taurine derivatives are described notably by Kontro et al. (1983) and by Andersen et al. (1984). Derivatives include for instance taurolidine (4,4'-methylene-bis(tetrahydro-2H-1,2,4-thiadiazine-1,1-dioxide or taurolin), taurultam and taurinamide, chlorohydrate-N-isopropylamide-2-(1-phenylethyl)amino ethanesulfonic acid. Non-limiting examples of taurine analogs include (+/−) piperidine-3-sulfonic acid (PSA), 2-aminoethylphosphonic acid (AEP), (+/−) 2-acetylaminocyclohexane sulfonic acid (ATAHS), 2-aminobenzenesulfonate (ANSA), hypotaurine, .+−.trans-2-aminocyclopentanesulfonic acid (TAPS) 8-tetrahydroquinoleine sulfonic acid (THQS), N-2-hydroxyethylpiperazine-N'-2-ethane sulphonic acid (HEPES), beta-alanine, glycine, guanidinoethylsulfate (GES), 3-acetamido-1-propanesulfonic acid (acamprosate). Non-limiting examples of substances required for taurine biosynthesis are selected from the group consisting of vitamin B6 (or pyridoxal-5'-phosphate), vitamin B12 (cobalamin), folic acid, riboflavin, pyridoxine, niacin, thiamine (thiamine pyrophosphate) and pantothenic acid. Any of these specific compounds may be employed in the practice of the invention.

Subjects suitable for methods of the invention include both human patients and non-human mammals. Preferably, the methods of the invention are directed to treating human subjects. In general, a "therapeutically effective amount", or "effective amount", or "therapeutically effective", as used herein, refers to that amount which provides a therapeutic effect for a given condition and administration regimen. This is a predetermined quantity of active material calculated to produce a desired therapeutic effect in association with the required additive and diluent; i.e., a carrier, or administration vehicle. Further, it is intended to mean an amount sufficient to reduce and most preferably prevent a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluents; i.e., carrier, or additive.

Other than taurine, the OPC differentiation-inducing agents may also be administered to the subject via a pharmaceutical composition. OPC differentiation-inducing agents suitable for the invention include any compounds that are capable of stimulating or promoting the differentiation of OPCs into oligodendrocytes. For example, the employed OPC differentiation-inducing agent can be an agent selected from any of the following classes of agents: M1 antagonists, M3 antagonists, H3 antagonists/inverse agonists, thyroid hormone receptor agonists, ER beta specific inhibitors, selective estrogen receptor modulators, delta 8,9 sterols, GPR56 agonists, PPAR gamma agonists, RXR agonists, sigma-1 receptor agonists, antifungal agents and gamma secretase inhibitors. See, e.g., Kremer et al., Trends Neurosci., 39:246-263, 2016; WO2012/112933; Mei al., *J. Neurosci.* 36, 7925-7935 (2016); Najm et al., *Nature* 522, 216-220 (2015); Buckley et al., *Neuropharmacol.* 59, 149-159 (2010); Deshmukh et al., *Nature* 502, 327-332 (2013); and Mei et al., *Nat. Med.* 20, 954-960 (2014). In some embodiments, the employed OPC differentiation-inducing agent can be one that induces OPC differentiation by acting as M1 antagonists. In some embodiments, the employed OPC differentiation-inducing agents can be one that induces OPC differentiation via another mechanism or pathway noted above. In various embodiments, the employed OPC differentiation-inducing agents can be anti-muscarinics (e.g., clemastine, benztropine); triiodothyronine (T3), thyroid hormone mimetics and beta-selective thyroid hormone mimetics (e.g., sobetirome and derivatives thereof); estrogen receptor modulators (e.g., ERbeta agonists indazole); azole antifungals (e.g., miconazole); corticosteroids such as clobetasol; 8,9-unsaturated sterols and inhibitors of CYP51, TM7SF2, or EBP (which lead to the accumulation 8,9-unsaturated sterols); RXR-gamma agonists (e.g., IRX4204); H3 antagonists (e.g., GSK239512).

The pharmaceutical compositions to be administered to the subject can further include another agent that is known for enhancing remyelination and for treating demyelinating diseases. Thus, in some embodiments, taurine and an OPC differentiation-inducing agent can be used in combination with a known demyelinating disease treatment or a known disease-modifying therapy. In some of these embodiments, a known demyelinating disease-modifying drug is used. Examples of such drugs include, e.g., IFN-beta1a, IFN-beta1b, glatiramer acetate, natalizumab, alemtuzumab, ocrelizumab, teriflunomide, dimethyl fumarate, cladribine, and fingolimod. In some other embodiments, the employed known drug for treating demyelinating diseases are agents targeting a S1P receptor. As detailed below, many known immunomodulators targeting S1P receptors can be employed in the practice of the invention. In addition, any of the different classes of OPC differentiation-inducing agents can be used in these combination therapies of the invention. In some specific embodiments, the subject can be treated with taurine and an OPC differentiation-inducing agent as exemplified herein (e.g., T3, benztropine, clemastine or miconazole). In some other specific embodiments, the subject can be treated with taurine and a S1P receptor agonist, as well as an OPC differentiation-inducing agent such as T3, benztropine or miconazole.

S1P receptors are validated targets for treating targets for demyelinating diseases such as MS. Many S1P receptor agonists known in the art and their variants can readily employed in the practice of the methods of the invention. In some preferred embodiments, the S1P receptor agonist used in the invention is selective for S1PR1. See, e.g., Subei et al., CNS Drugs. 29(7): 565-575, 2015; Roberts et al., Expert Opin. Ther. Pat. 23(7):817-41, 2013; Gonzalez-Cabrera et al., Mol. Pharmacol. 74(5):1308-18, 2008; Schuchardt et al., Br. J. Pharmacol. 163: 1140-1162, 2011; Tsukada et al., J. Cardiovasc. Pharmacol. 50(6):660-9, 2007; Komiya et al., Clin. Exp. Immunol. 171, 54-62, 2013; Zhang et al., J. Neuroimmunol. 216:59-65, 2009; Jin et al., Biochem. Pharmacol. 90(1):50-61, 2014; Pan et al., Chem Biol. 13:1227-34, 2006; Demont et al., ACS Med. Chem. Lett. 2: 444-449, 2011; Bolli et al., J. Med. Chem., 57: 110-130, 2011; Gergely et al., Br. J. Pharmacol. 167, 1035-1047, 2012; Bolli et al., J. Med. Chem. 53, 4198-4211, 2010; Nishi et al., ACS Med. Chem. Lett. 2, 368-372, 2011; Seo et al., J. Immunol. 188(10): 4759-4768, 2012; Cahalan et al., Nat. Chem. Biol. 7(5): 254-256, 2011; Shimizu et al., Circulation 111, 222-229, 2005; Aguilar et al., Bioorg. Med. Chem. Lett. 22, 7672-7676, 2012; and WO2009/151529.

In some embodiments, S1P receptor agonists used in the invention are S1PR1 agonists. Specific examples of S1PR1 agonists that can be used in the invention include, e.g., MT1303, ACT-128800, BAF312, GSK2018682, CYM-5442, ONO-4641, AUY954, RG3477, SEW-2871, CS-0777, Syl930, AAL-R, RPC1063, RP-001, KRP-203, FTY720 (aka fingolimod), siponimod, ponesimod, and thiophenes derivatives. Structures and functions of these compounds have been well characterized in the art. They can all be obtained either from commercial sources or via de novo synthesis using standard protocols that have been reported in the art. In some embodiments, the S1PR1 agonist used in the invention is selective for S1PR1 over the other S1P receptors. Examples of such S1P modulators include MT1303, RPC1063, ACT-128800, ONO-4641, BAF312, GSK2018682, and FTY720. These compounds are all known and well characterized in the art. See, e.g., Subei et al., CNS Drugs. 29(7): 565-575, 2015. In some embodiments, the methods of the invention can use the CYM-5442 compound. This compound can be purchased from commercial vendors such as Krackeler Scientific (Albany, N.Y.) or generated using synthesis scheme as described in the art, e.g., Gonzalez-Cabrera et al., Mol. Pharmacol. 74:1308-1318, 2008; and WO2009/151529.

Benztropine is an anticholinergic drug used in patients to reduce extrapyramidal side effects of antipsychotic treatment. Benztropine is also a second-line drug for the treatment of Parkinson's disease. It improves tremor and may alleviate rigidity and bradykinesia. Benztropine is also sometimes used for the treatment of dystonia, a rare disorder that causes abnormal muscle contraction, resulting in twisting postures of limbs, trunk, or face. In veterinary medicine, benztropine is used to treat priapism in stallions.

In another aspect, the invention provides methods for promoting OPC differentiation into oligodendrocytes with a combination of taurine and an OPC differentiation-inducing agent. The methods entail contacting an OPC or population of OPCs with an effective amount of taurine or a taurine-like compound plus any of the OPC differentiation-inducing agents as described herein. In certain embodiments, the OPCs are human OPCs. Generally speaking, an "effective amount" refers to that amount that achieves a desired effect. As is appreciated by those skilled in the art, the amount of a compound may vary depending on its specific activity. Suitable amounts may contain a predetermined quantity of active composition calculated to produce the desired effect either alone or when used in combination with one or more additional agents. In certain embodiments, OPCs are contacted with an amount or concentration of taurine or taurine-like compound sufficient to enhance OPC differentiation into oligodendrocytes. For example, in particular embodiments, the percentage of OPCs that differentiate into oligodendrocytes within a population of OPCs contacted with taurine or the taurine-like compound is at least 10%, at least 20%, at least 30%, at least 40%, at least 50%, at least 60%, at least 70%, at least 80%, at least 90%, at least 100%, at least two-fold, at least three-fold, at least five-fold, at least ten-fold, or at least twenty-fold greater than the percentage of OPCs that differentiate into oligodendrocytes within a population of OPCs not contacted with taurine or the taurine-like compound.

As exemplified herein, taurine can enhance drug-induced OPC differentiation into mature oligodendrocytes. Taurine is also able to promote cell survival and decrease apoptosis in oligodendrocyte differentiation. Accordingly, the present disclosure also provides methods for promoting survival and/or inhibiting apoptosis of OPCs, e.g., during differentiation into oligodendrocytes. The methods involve contacting the OPCs with an effective amount of taurine or a taurine-like compound.

In some embodiments, the methods of the invention can be performed in vitro with cultured OPCs. In the practice of these methods, the OPCs can be generated from stem cells. For example, pluripotent stem cells or induced neural stem cells (DNSCs) can be used for generation of OPCs. See, e.g., Kim et al., Exp. & Mol. Med. 49: e361, 2017; and Lee et al., Front Cell Neurosci. 12: 198, 2018. To promote OPC differentiation, the cells are contacted with taurine under appropriate condition to allow the compound exert its effect on the differentiation of OPCs. Other than taurine, the cultured OPCs can be additionally contacted with an agent that is known to promote OPC differentiation, e.g., T3, benztropine or miconazole as described herein. In some other embodiments, the methods of promoting OPC differentiation into oligodendrocytes can be performed in vivo inside a subject. For in vivo application, a subject can be administered with taurine via a suitable pharmaceutical composition. In some of these embodiments, the subject can be one who is afflicted with or at risk of developing a demyelinating disease such as MS. Taurine and taurine-like compounds may be administered to a subject by any known route of administration, including but not limited to parenteral or oral administration, e.g., intravenously. They may be administered systemically or locally. In some embodiments, taurine is administered to the subject via targeted delivery, e.g., targeted delivery to OPCs in the central nervous system.

By promoting OPC differentiation into mature oligodendrocytes, the methods of the invention can be used in many research and clinical settings. For example, the methods can facilitate studies at understanding human oligodendrocyte biology and the process of myelination. Patient-specific OPCs can be generated for the study of demyelinating or dysmyelinating disorders, such as MS, adrenoleukodystrophy, vanishing white matter disease, Pelizaeus-Merzbacher disease and all leukodystrophies. Furthermore, a crucial role for oligodendrocytes is emerging in many other neurodegenerative and neurological disorders, including amyotrophic lateral sclerosis, Huntington's disease, Alzheimer's disease and schizophrenia. Human OPCs can be used to develop in vitro myelination assays, to screen for myelinating compounds, and ultimately to become a source for autologous cell replacement therapies.

The present invention also provides pharmaceutical compositions that contain taurine or a taurine-like compound, or the combination of drugs described above. These pharmaceutical compositions can be used for the prevention and treatment of demyelinating diseases such as multiple sclerosis (MS). In the pharmaceutical compositions of the invention, the amount of the taurine or a taurine-like compound, is adapted so that the said pharmaceutical composition is adapted so that the dosage form used allows the administration of an amount of taurine or of the taurine-like compound ranging from 10 µg to 10 grams per day for a human adult patient having a mean weight of 80 kilos. In some pharmaceutical compositions, the active ingredient is used in combination with one or more pharmaceutically or physiologically acceptable excipients. Generally, a pharmaceutical composition according to the invention comprises an amount of excipient(s) that ranges from 0.1% to 99.9% by weight, and usually from 10% to 99% by weight, based on the total weight of the said pharmaceutical composition. By "physiologically acceptable excipient or carrier" is meant solid or liquid filler, diluents or substance which may be safely used in systemic or topical administration. Depending on the particular route of administration, a variety of pharmaceutically acceptable carriers well known in the art include solid or liquid fillers, diluents, hydrotropes, surface active agents, and encapsulating substances.

Pharmaceutically acceptable carriers for systemic administration that may be incorporated in the composition of the invention include sugar, starches, cellulose, vegetable oils, buffers, polyols and alginic acid. Specific pharmaceutically acceptable carriers are described in the following documents, all incorporated herein by reference: U.S. Pat. No. 4,401,663, Buckwalter et al. issued Aug. 30, 1983; European Patent Application No. 089710, LaHann et al. published Sep. 28, 1983; and European Patent Application No. 0068592, Buckwalter et al. published Jan. 5, 1983. Preferred carriers for parenteral administration include propylene glycol, pyrrolidone, ethyl oleate, aqueous ethanol, and combinations thereof.

Representative carriers include acacia, agar, alginates, hydroxyalkylcellulose, hydroxypropyl methylcellulose, carboxymethylcellulose, carboxymethylcellulose sodium, carrageenan, powdered cellulose, guar gum, cholesterol, gelatin, gum agar, gum arabic, gum karaya, gum ghatti, locust bean gum, octoxynol 9, oleyl alcohol, pectin, poly(acrylic acid) and its homologs, polyethylene glycol, polyvinyl alcohol, polyacrylamide, sodium lauryl sulfate, poly(ethylene oxide), polyvinylpyrrolidone, glycol monostearate, propylene glycol monostearate, xanthan gum, tragacanth, sorbitan esters, stearyl alcohol, starch and its modifications. Suitable ranges vary from about 0.5% to about 1%.

Pharmaceutical compositions of the invention can be prepared in accordance with methods well known and routinely practiced in the art. See, e.g., Remington: *The Science and Practice of Pharmacy*, Mack Publishing Co., 20$^{th}$ ed., 2000. As noted above, a therapeutically effective amount of each of the active ingredients (e.g., taurine or taurine-like compound, the OPC differentiation-inducing agent, and the known demyelinating disease drug or modifying agent) should be included in the pharmaceutical composition. The selected dosage level for each of the active ingredients depends upon a variety of pharmacokinetic factors including the activity of the particular composition of the present invention employed, the route of administration, the time of administration, and the rate of excretion of the particular compound being employed. It also depends on the duration of the treatment, other drugs, compounds and/or materials used in combination with the particular compositions employed, the age, gender, weight, condition, general health and prior medical history of the subject being treated, and like factors. Determination of optimal dosages can be based on well-known protocols as described in the art and the specific exemplifications provided herein. See, e.g., Remington: *The Science and Practice of Pharmacy*, Mack Publishing Co., 20$^{th}$ ed., 2000. For a given active ingredient used in the therapeutic embodiments of the invention, one skilled in the art can easily identify the effective amount by using routinely practiced pharmaceutical methods. Dosages used in vitro or animal studies may provide useful guidance in the amounts useful for in vivo administration of the pharmaceutical composition, and animal models may be used to determine effective dosages for treatment of particular disorders. Typically, a pharmaceutically effective dosage would be between about 0.001 and 150 mg/kg body weight of the subject to be treated. In various embodiments, a subject in need of treatment can be administered a daily dosage for taurine or taurine-like compound in the range of from about 50 mg to about 8 g, from about 100 mg to about 4 g, or from about 250 mg to about 2 g. For the other active ingredients such as OPC differentiation-inducing agents benztropine or clemastine, the subject can be administered a daily dosage in the range of from about 1 mg to about 20 mg, from about 2 mg to about 10 mg, or from about 4 mg to about 6 mg. Thus, as exemplification, a pharmaceutical composition containing a combination of taurine and clemastine can have a target dose of around 500 mg to 4 g of taurine and around 4 mg to 8 mg of clemastine per day, and a pharmaceutical composition containing a combination of taurine and benztropine can have a target dose of around 500 mg to 4 g of taurine and around 2 mg to 6 mg of benztropine per day. Optimal dosages for various compounds (e.g., taurine-like compounds, other OPC differentiation-inducing agents and S1P receptor agonists) can also be readily determined in accordance with guidance that have been reported in the art for the specific compounds. See, e.g., Kremer et al. (Trends Neurosci., 39:246-263, 2016) and references cited therein. For in in vitro methods described herein, concentrations of the different compounds (e.g., taurine or taurine-like compound, and OPC differentiation-inducing agents) can also be determined in accordance with the protocols exemplified herein or published literatures in the relevant arts. See, e.g., *Taurine in Health and Disease*, Huxtable and Michalk (Eds.), Springer Science & Business Media, New York (1994); Kremer et al., Trends Neurosci., 39:246-263, 2016; and WO2012/112933.

Pharmaceutical compositions containing taurine or taurine-like compounds and the other compounds described herein (e.g., OPC differentiation-inducing agents) are usually administered to the subjects on multiple occasions. Intervals between single dosages can be daily, weekly, monthly or yearly. Intervals can also be irregular as indicated by measuring blood levels of the relevant compounds and the other therapeutic agents used in the subject. In some methods, dosage is adjusted to achieve a plasma compound concentration of 1-1000 µg/ml, and in some methods 25-300 µg/ml or 10-100 µg/ml. Measured differently, administration of the pharmaceutical composition to the subject should achieve an effective local concentration of the active ingredient in the subject. For example, a taurine concentration of at least 1 mM, at least 2 mM, at least 5 mM, at least 10 mM or higher should be achieved in the CNS of the subject. In some embodiments, the therapeutic agents can be administered as a sustained release formulation, in which case less frequent administration is required. Dosage and frequency vary depending on the half-life of the inhibitor compound and the other drugs in the subject. The dosage and frequency of administration can vary depending on whether the treatment is prophylactic or therapeutic. In prophylactic applications, a relatively low dosage is administered at relatively infrequent intervals over a long period of time. Some subjects may continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime.

For formulating a pharmaceutical composition according to the invention, the one skilled in the art will advantageously refer to the last edition of the European pharmacopoeia or of the United States pharmacopoeia. Preferably, the one skilled in the art can refer to the fifth edition of the *European Pharmacopoeia*, or also to the edition USP 28-NF23 of the *United States Pharmacopoeia*. Pharmaceutical composition according to the invention may also contain other compounds, which may be biologically active or inactive as described herein. For example, substance according to the invention may be combined with another agent, in a treatment combination, and administered according to a treatment regimen of the present invention. Such combinations may be administered as separate compositions, combined for delivery in a complementary delivery system, or formulated in a combined composition, such as a mixture or a fusion compound.

In a related aspect, the invention provides medical uses of the pharmaceutical compositions of the invention or various combinations of compounds described here for treating or ameliorating symptoms of demyelinating diseases, for increasing myelination in the CNS, or for promoting OPC differentiation in vitro or in vivo. The invention also provides kits for carrying out the therapeutic applications disclosed herein. For example, the invention provides therapeutic kits for use in the treatment of demyelinating diseases such as MS. The kits can also be used for promoting OPC differentiation into oligodendrocytes. The therapeutic kits of the invention typically contain taurine as active agent and optionally one or more of the other therapeutic compounds described herein (e.g., S1P receptor agonists, T3, benztropine and miconazole). The kits can optionally contain suitable pharmaceutically acceptable carriers or excipients for administering the active agents. The therapeutic kits can further include packaging material for packaging the reagents and a notification in or on the packaging material. The kits can additionally include appropriate instructions for use and labels indicating the intended use of the contents of the kit. The instructions can be present on any written material or recorded material supplied on or with the kit or which otherwise accompanies the kit.

EXAMPLES

The following examples are offered to illustrate, but not to limit the present invention.

Example 1: Global Comparative Metabolomic Analysis

Using mass spectrometry-based untargeted metabolomics and lipidomics with hydrophilic interaction chromatography (HILIC) and reversed phase liquid chromatography (RP) respectively combined with electrospray ionization quadruple time-of-flight mass spectrometry (LC-ESI-QTOF-MS), we characterized differentially regulated metabolites from OPCs and mature oligodendrocyte (OL) cells (FIG. 6). Using established conditions for the in vitro differentiation of purified primary OPC cultures generated by immunopanning of rat optic nerves (Deshmukh et al., Nature 502, 327-332, 2013), cells were differentiated over the course of 6 days to a mature myelin basic protein positive (MBP$^+$) fate using triiodothyronine (T3), a known inducer of OPC differentiation (Fernandez et al., *Proc Natl Acad Sci. US* 101, 16363-16368, 2004). Metabolomics analysis was performed on normalized lysates derived from OPCs cultured for 6 days in basal media (2 ng/mL PDGFαα) containing T3 or DMSO vehicle. Western blot-based analysis of MBP in lysates derived from parallel cultures was used to confirm relative differentiation efficiency. Consistent with previous studies of ESC cultures (Yanes et al., Nat. Chem. Biol. 6, 411-417, 2010), RP lipidomics showed more altered lipids with a highly unsaturated degree in OPCs, compared with those in the OLs (FIG. 7). Using HILIC-based metabolomics analysis, we evaluated metabolites associated with cellular respiration, which, as described above, have previously been found to play essential roles in cellular differentiation processes (Folmes et al., Cell Metab 14, 264-271, 2011). Mature OLs were found to have many altered features when compared with immature OPCs, with over 100 features identified following manual filtering. Most of these features were found to be unregulated in the mature OL population. Amongst 22 identified metabolites associated with respiration and redox processes, glycolysis, TCA cycle, nucleoside, pyrimidine and purine biosynthesis pathways were all significantly enriched (FIG. 1a). This observation is also consistent with previous studies investigating the differences between iPSCs and somatic cells. Further, levels of central carbon metabolites, including tricarboxylic acids as well as pyrimidine and purine nucleotides, decrease significantly when somatic cells are reprogrammed to iPSCs (Panopoulos et al., Cell Res 22, 168-177, 2012), suggesting some overlap between the proliferating metabolomic states of OPCs and iPSCs.

As mentioned, changes in oxidative status are associated with and play an important role in cellular reprogramming and differentiation. When mammalian cells are exposed to increased oxidative stress, the GSH/GSSG ratio decreases as GSH is converted to oxidized glutathione (GSSG). Thus, we quantified GSH/GSSG to evaluate the oxidation status change over the course of OPC differentiation. As shown in FIG. 8, a substantial decrease in the GSH/GSSG ratio was observed in OLs compared to OPCs. These observations suggest that redox regulation could be an important factor mediating OPC differentiation and/or OL maturation.

Example 2. Targeted Metabolomic Pathway Analysis

Intriguingly, taurine and creatine pathways were found to be the most highly altered events associated with OPC differentiation. Taurine and hypotaurine increased by over 20- and 10-fold, respectively, and metabolites in the creatine pathway were also upregulated by at least an order of magnitude (FIG. 1a). A targeted analysis of ~20 metabolites upstream and downstream of the taurine and creatine pathways was performed using triple-quadrupole MS (QQQ-MS) in multiple reaction monitoring (MRM) mode to increase the sensitivity and examine additional metabolites associated with these pathways (FIG. 1b). Metabolites from both pathways were found to be upregulated in differentiated OLs, consistent with global metabolomic analyses. Specifically, creatine, creatinine and phosphocreatine, as well as taurine, hypotaurine and taurocyamine were all found to be ~4-5-fold upregulated in differentiated OLs (FIG. 1b), based on targeted quantitative analysis. The upstream metabolite cysteine was significantly (~4-fold) decreased in mature OLs, consistent with it serving as a primary precursor of taurine (FIG. 1b). Overall, results derived from targeted metabolomic analysis were consistent with the findings of the global metabolomics study, with more metabolites along the relevant pathways being observed at differentiable levels.

Example 3. Impact of Exogenously Supplemented Metabolites

To examine their physiological function and determine their potential impact on the OPC differentiation process, several of the most altered metabolites associated with OPC differentiation, including taurine, hypotaurine, creatine, and phosphocreatine (PCr), were supplemented to basal and drug-induced differentiation conditions at three physiologically relevant concentrations (0.2, 2, and 20 mM). Compounds were added alone or as mixtures in the presence or absence of optimal or suboptimal concentrations of the known OPC differentiation-inducing drugs benztropine or miconazole. Importantly, while both of these drugs have been demonstrated to induce OPC differentiation in vitro and in vivo, the observed maximal in vitro efficacy of both drugs is suboptimal when compared to that observed for T3. When evaluated in the absence of benztropine or miconazole, no significant effect was observed for any combination or single metabolite. However, when added to either benztropine- or miconazole-containing media, taurine was found to dramatically increase the efficacy of induced OPC differentiation (FIG. 2*a-d*). Specifically, MBP induction, as determined by Western blot analysis, was increased by 2.3- and 2.0-fold, respectively, following addition of 2 mM taurine when compared to miconazole- or benztropine-induced differentiation in the absence of taurine supplementation (FIGS. 2*a* and *b*, FIGS. 9*a* and *b*). In addition to OPC differentiation induced by benztropine or miconazole, similar results were also obtained with taurine on clemastine-induced oligodendrocyte maturation (FIG. 15). Other than taurine, creatine and PCr also showed some additive effects, however, interpretation of results derived from creatine supplementation were confounded by its essential pre-existing presence in media used for the culture and differentiation of OPCS.

Figure 3:
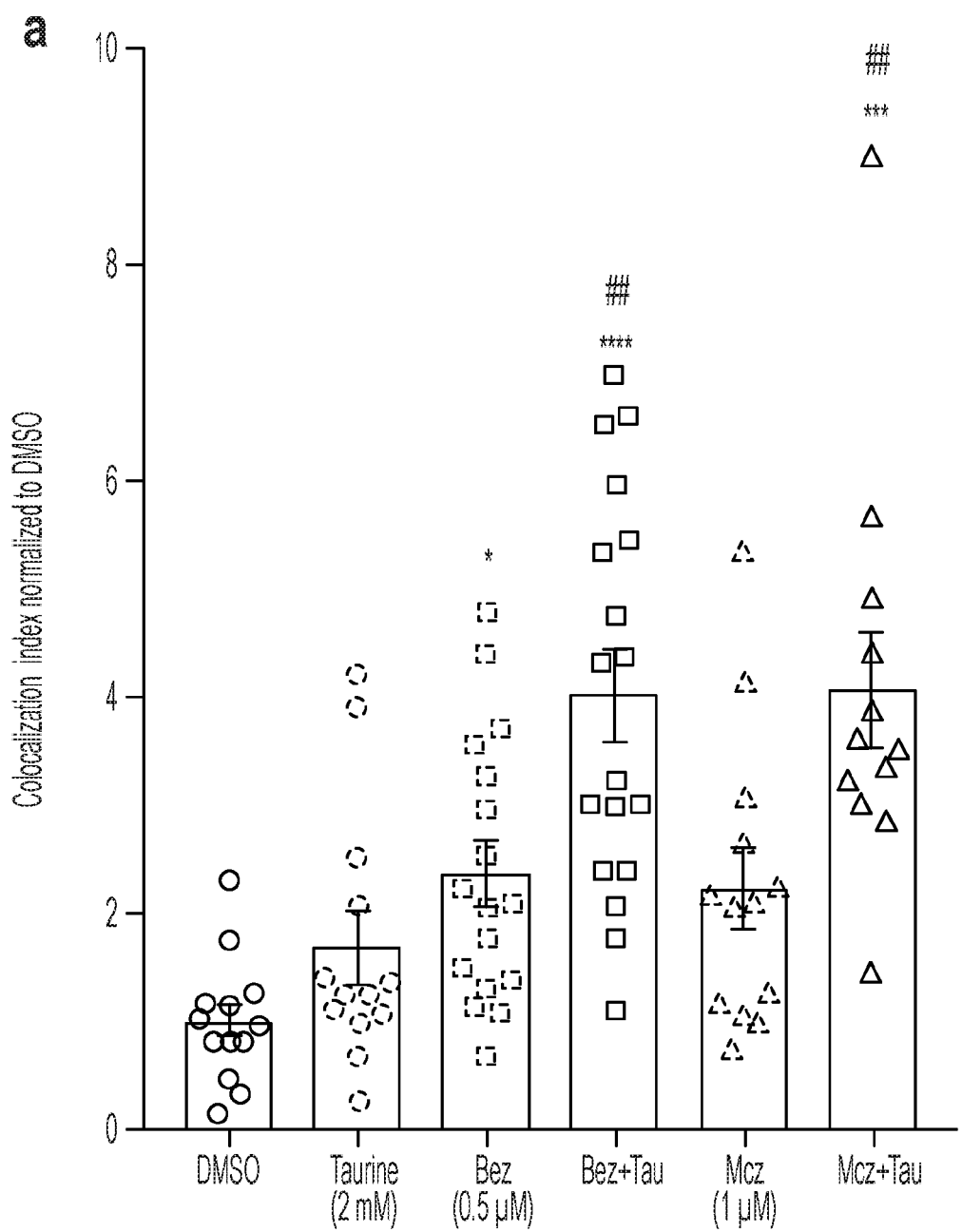
FIG. 3 shows impact of taurine treatment on observed indices of MBP-colocalization with co-cultured axons. Shown in the figure is quantification of MBP-colocalization with the axons of primary mouse cortical neurons co-cultured with OPCs following 14 days of treatment. Cultures were treated with 0.5 µM benztropine or 1 µM miconazole in the presence or absence of 2 mM taurine. The data are mean±SEM (*=significance of treatments vs. DMSO; #=significance of co-treatment vs. drug alone; one symbol: $p<0.05$, two symbols: $p<0.01$, four symbols: $p<0.0001$) (n=13 technical replicates, DMSO, Tau, Mcz, Mcz+Tau; n=17 technical replicates, Bez; n=19 technical replicates, Bez+Tau). "Bez", "Mcz" and "Tau" are the abbreviations for "benztropine", "miconazole" and "taurine"; respectively.

Using an established high content imaging assay (Deshmukh et al., Nature 502, 327-332, 2013), based on MBP expression, matrices of 10 concentrations each of taurine and miconazole or benztropine were evaluated to determine optimal combination treatment conditions. In addition to confirming the overall enhancement of induced-differentiation that was observed by Western blot-based analysis, the results of the high content imaging analysis indicate that addition of >2 mM taurine also enhances overall cell number by over 20% when compared to drug treatment alone (FIGS. 9*c* and *d*). Further, we evaluated the impact of exogenous taurine addition on drug-induced OL maturation and function, using an established confocal microscopy-based imaging assay involving co-cultured primary mouse cortical neurons (Deshmukh et al., Nature 502, 327, 2013). Following 14 days of neuron-OPC co-culture, 2 mM taurine was found to significantly increase the observed index of MBP-colocalization with axons in cultures treated with either benzotropine or miconzole to induce OPC differentiation (FIG. 3).

Example 4. Differentiation State-Dependent Effects of Taurine

During the course of in vitro and in vivo OPC differentiation, cells transition though an immature MBP⁻ "premyelinating" oligodendrocyte state. In our assay system, this occurs between day 2 and 3 of differentiation. To determine the stage of OPC differentiation at which taurine enhances drug efficacy, we tested the effect of taurine at various time points, by initiating dosing with taurine at Days 0 to 5 and evaluating cell cultures at Day 6. The most significant impact on MBP expression was observed by adding taurine between days 1 and 3, with addition on day 0 being significantly less efficacious (FIG. 10a-b), which suggests that taurine facilitates the maturation of pre-myelinating OLs rather than inducing cell cycle exit and/or the differentiation of fully immature proliferating OPCs. Consistently, addition of taurine to basal (DMSO vehicle) or drug-induced differentiation conditions on day 0, 1 or 3 was found to have a minimal, albeit statistically significant, impact on the number of residual immature $A2B5^+$ OPCs at days 3 or day 6 (FIG. 10c-d). This temporal trend also coincided with the decrease of the oxidative stress marker GSH/GSSG at Day 3 (FIG. 8).

Example 5. Impact of Taurine on Mitochondrial Function

Figure 4:
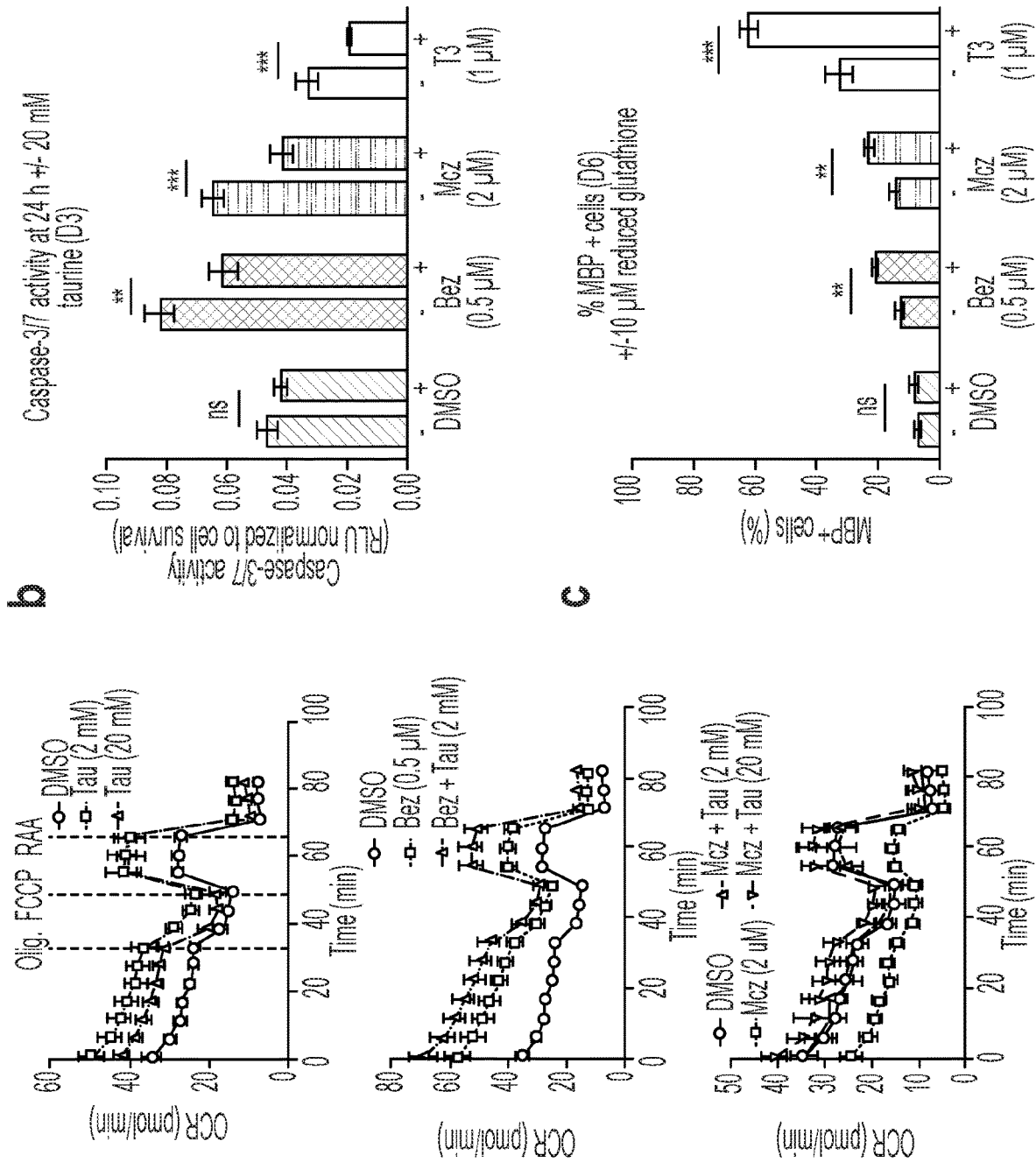
FIG. 4 shows impact of taurine treatment on OL mitochondrial function and role of redox state on OPC differentiation. (a) Oxygen consumption rate (OCR: pmol/min) of OPCs (40,000 cells/well) treated for 6 days with taurine (2 and 20 mM) and DMSO, benztropine (0.5 µM) with and without 2 mM taurine or Miconazole (2 µM) with and without 2 and 20 mM taurine. Complex activity was measured at baseline and after the successive addition of 1 µM oligomycin (Olig.), 2 µM carbonyl cyanide 4-(trifluoromethoxy) phenylhydrazone (FCCP) and 2 µM rotenone and antimycin A (RAA). The data are mean±SD (n=12 technical replicates). The dashed line in the top panel indicates the addition of the compound indicated. "Tau", "Bez" and "Mcz" are the abbreviations for "taurine", "benztropine" and "Miconazole"; respectively. (b) Quantification of Caspase-3/7 activation 24 h post-taurine addition on day 3 (D3), after treatment with DMSO, Miconazole (2 µM), benztropine (0.5 µM), or T3 (1 µM) on day 0. Data are mean±SD of the luminescence (RLU) normalized to corresponding cell survival per well (n=3 replicate cell cultures). (c) Quantification of MBP-positive OLs based on MBP immunofluorescent analysis on day 6 (D6) post-treatment with DMSO, Miconazole (2 µM), benztropine (0.5 µM), or T3 (1 µM), following co-treatment with or without reduced glutathione (10 µM). Data are mean±SD for the percentage of MBP-positive cells per well (n=3 replicate cell cultures). "ns", "", and "*" represent no significance, $p<0.01$, and $p<0.001$; respectively.

In addition to its ability to function in the maintenance of buffer capacity, redox potential, osmoregulation and membrane stabilization, taurine can modulate ion flux and act as a neuromodulator to control synaptic transmission and enhance or preserve mitochondrial function in response to increased secondary metabolite demand or exicitotoxicity. Specifically, taurine has been demonstrated to be able to regulate intracellular calcium levels and preserve mitochondrial energy metabolism in glutamate challenged cultures of cerebellar granule cells. When proliferating OPCs differentiate to OLs that function to produce myelin, mitochondrial energy requirements would presumably be challenged in response to the activation of phospholipid biosynthetic pathways. We therefore examined oxygen consumption rates (OCR) associated with mitochondrial respiratory activity using an XFe96 Seahorse instrument. Addition of 2 mM taurine to culture media was found to significantly increase OCR values at day 6 under basal, as well as benztropine- or miconazole-induced differentiation conditions (FIG. 4a). Interestingly, miconazole treatment alone was found to have a negative impact on OCR values when compared to DMSO or benztropine treatment (FIG. 4a). These observations are consistent with the ability of taurine to enhance mitochondrial function in both OPCs and OLs. Consistent with the critical dependence of OPCs and OLs on mitochondrial function, treatment with the mitochondrial function inhibitors oligomycin or rotenone induced cell death within 24 hours at all concentrations tested, which precluded the ability to evaluate the impact of taurine rescue following treatment with these agents in the differentiation assay.

Example 6. Impact of Taurine on OPC and OL Survival

Related to a beneficial impact on the process of mitochondrial function, the observed overall differentiation enhancing effect of taurine could be derived from a protective effect associated with inhibition of apoptosis. Significant apoptosis would be expected to occur as OPCs exit the cell cycle in response to growth factor withdrawal, as well as during the process of pre-oligodendrocyte maturation. As such, we evaluated the impact of taurine addition on cell survival and apoptosis over the course of the oligodendrocyte differentiation process using Cell Titer Glo and Caspase Glo 3/7 assays. When added at day 0 (FIG. 11a, FIG. 11c) or day 3 (FIG. 4b, FIG. 11b, FIG. 11d), taurine was found to decrease Caspase 3/7 activation 24 hours following supplementation under drug-induced differentiation conditions (i.e., 1 µM T3, 0.5 µM benztropine or 2 µM miconazole). This finding is consistent with the observed beneficial impact on overall survival at day 6, described above (FIG. 10). Taurine was also found to significantly inhibit apoptosis in OPCs treated with staurosporine, which served as a positive control for apoptosis induction (FIG. 11a-b). Taurine was not found to impact apoptosis or survival under basal (DMSO vehicle) differentiation conditions (FIG. 4b, FIG. 11a-b).

Example 7. Impact of Taurine on Oxidative Stress in OPCs and OLs

Oxidative stress has been demonstrated to disrupt oligodendrocyte differentiation by directly decreasing the expression of key pro-differentiation genes and increasing the expression of genes known to inhibit differentiation. Further, changes in intracellular redox state have even been reported to be sufficient to drive the balance between self-renewal and differentiation during the course of OL differentiation. We evaluated the potential impact of taurine-mediated redox state modulation on OL differentiation efficiency, by evaluating the impact of alternative reducing agents on basal (DMSO vehicle) or drug-induced OL differentiation. While reduced glutathione (10 µM GSH) (FIG. 4c) was found to have no significant effect on differentiation efficiency under basal conditions (DMSO), GSH (10 µM) was found to significantly enhance the overall efficiency of T3-induced differentiation (FIG. 4c), as well as observed total nuclei count (FIG. 12). Reduced glutathione was also found to enhance the overall efficiency of benztropine- or miconazole-induced differentiation, albeit to a lesser extent than what is observed following taurine addition (FIG. 4c) and the impact on total cell number was not found to be significant (FIG. 12). As such, modulation of redox state could be a beneficial contributing mechanism that serves to enhance the process of drug-induced OL differentiation. However, the inability to fully recapitulate the activity of taurine with alternative biological reducing agents indicates that this activity is not likely the sole mechanism by which taurine enhances the process of OL differentiation.

Example 8. Taurine-Induced Metabolomic Changes

To identify metabolic changes that are directly impacted by exogenous taurine supplementation in OPCs and OLs, binary global metabolomics analysis was performed between cell lysates following treatment with a given differentiation-inducing agent (i.e., T3, benztropine or miconazole) in the presence or absence of 20 mM taurine for 3 or 6 days. This pair-wise analysis allowed for the filtering out of drug-specific and differentiation state-dependent effects, thereby allowing for the identification of metabolomic changes that are specific to taurine supplementation. This analysis revealed that relatively few metabolite pools are impacted by taurine supplementation. However, significantly increased serine and cysteine pools were observed in lysates derived from taurine-treated OPCs, following 3 days of drug-induced differentiation using T3 (1 µM, 17.1- and 58.8-fold, respectively, FIG. 5a), benztropine (0.5 µM, 10.0- and 154.4-fold, respectively, FIG. 13a) or miconazole (2 µM, 19.4- and 76.5-fold, respectively, FIG. 13b). Similarly, at day 6, serine and cysteine levels were observed to be significantly higher in lysates derived from taurine-treated OPCs differentiated using T3 (1 μM, 2.1- and 26.6-fold, respectively, FIG. 5a), benztropine (0.5 μM, 13.4- and 44.7-fold, respectively, FIG. 14) or miconazole (2 μM, 92.5- and 47.2-fold, respectively, FIG. 14). Slightly higher GSH levels were observed in lysates derived from taurine treated OPCs differentiated using T3 (1 μM) at days 3 (1.8-fold, FIG. 5a) and day 6 (6.1-fold, FIG. 5a). Changes in GSH and glutamate were found be only minimally altered in benztropine (0.5 μM), or miconazole (2 μM) treated cultures at both time points (FIG. 13a-b). Collectively, the observed impacts on metabolite pools at different stages of the differentiation process imply that the addition of taurine reduces the need for serine and cysteine biosynthesis and/or increases available pools of these metabolites for alternative biosynthetic functions that are potentially required for OL maturation and/or function. Indeed, under optimal conditions of T3-induced differentiation, lower observed serine levels at day 6 following taurine supplementation, as compared to what is observed at day 3 (FIG. 5a), suggests that serine pools derived from taurine are consumed by other biosynthetic pathways in mature OLs.

Example 9. Direct Effect of Taurine on OPC Differentiation

Figure 5:
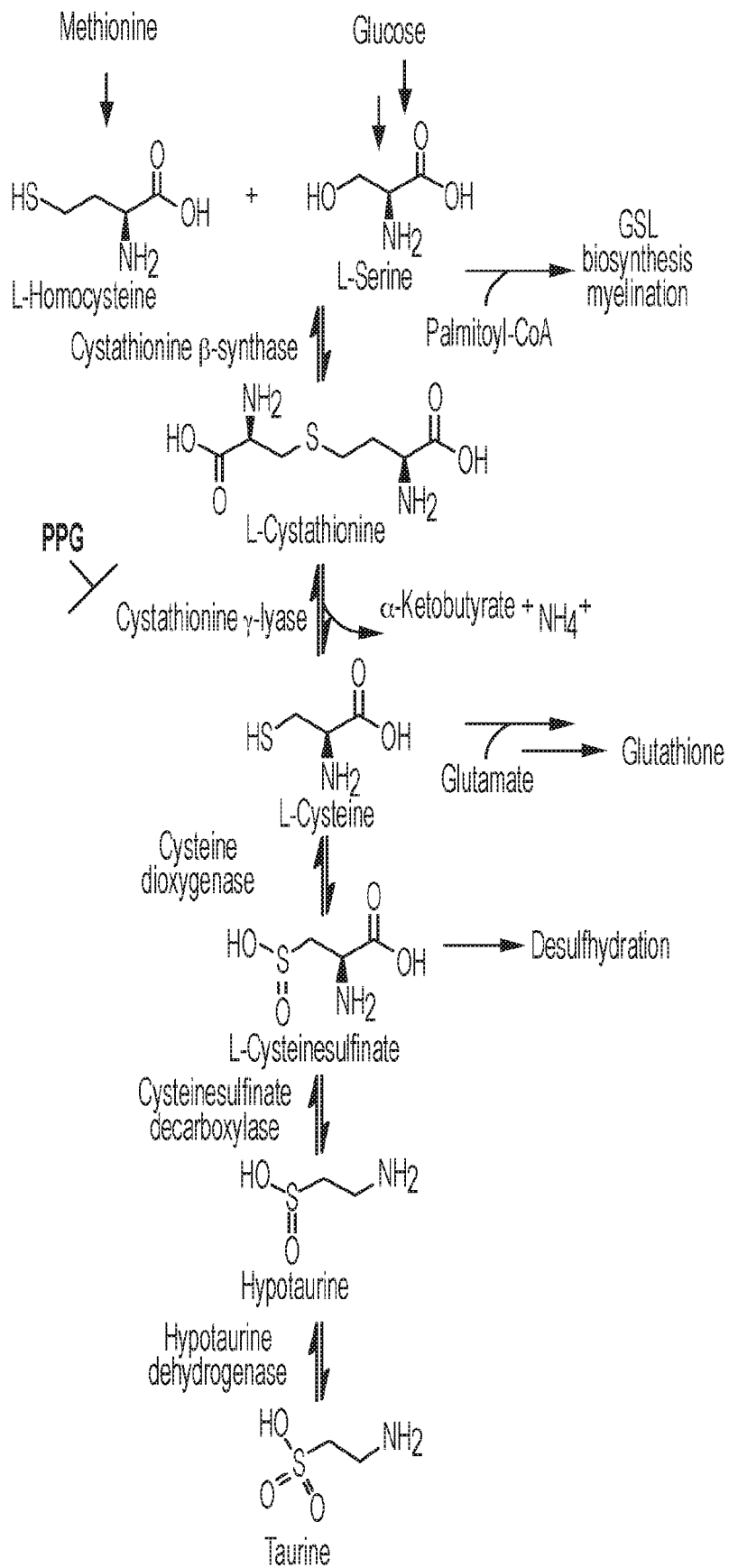
FIG. 5 shows binary global metabolomics analysis of taurine co-treatment and evaluation of the impact of inhibition of taurine biosynthesis on OL differentiation. (a) Binary global metabolomics analysis of the impact of taurine (20 mM) supplementation on pre-myelinating OLs (day 3, D3) and OLs (day 6, D6) differentiated using T3 (1 µM). Numbers represent fold changes of metabolites, with values smaller than one suggesting down-regulation and values larger than one suggesting up-regulation. White indicates non-detected (<LOD). Darker circles represent a p-value <0.05. (b) Taurine biosynthesis pathway highlighting the relationship to GSL biosynthesis and the impact of Proparglglycine (PPG)-mediated inhibition of cystathionine γ-lyase on taurine and GSH production. (c) Quantification of MBP-positive OLs based on MBP immunofluorescent analysis on day 6 post-treatment with DMSO, Miconazole (2 µM), benztropine (0.5 µM), or T3 (1 µM), following addition of PPG (10 µM), taurine (20 mM) or PPG (10 µM) and taurine (20 mM). "Bez", "Mcz" and "Tau" are the abbreviations for "benztropine", "miconazole" and "taurine"; respectively. Data are mean±SD for the percentage of MBP-positive cells per well (n=3 replicate cell cultures).
Figure 5:
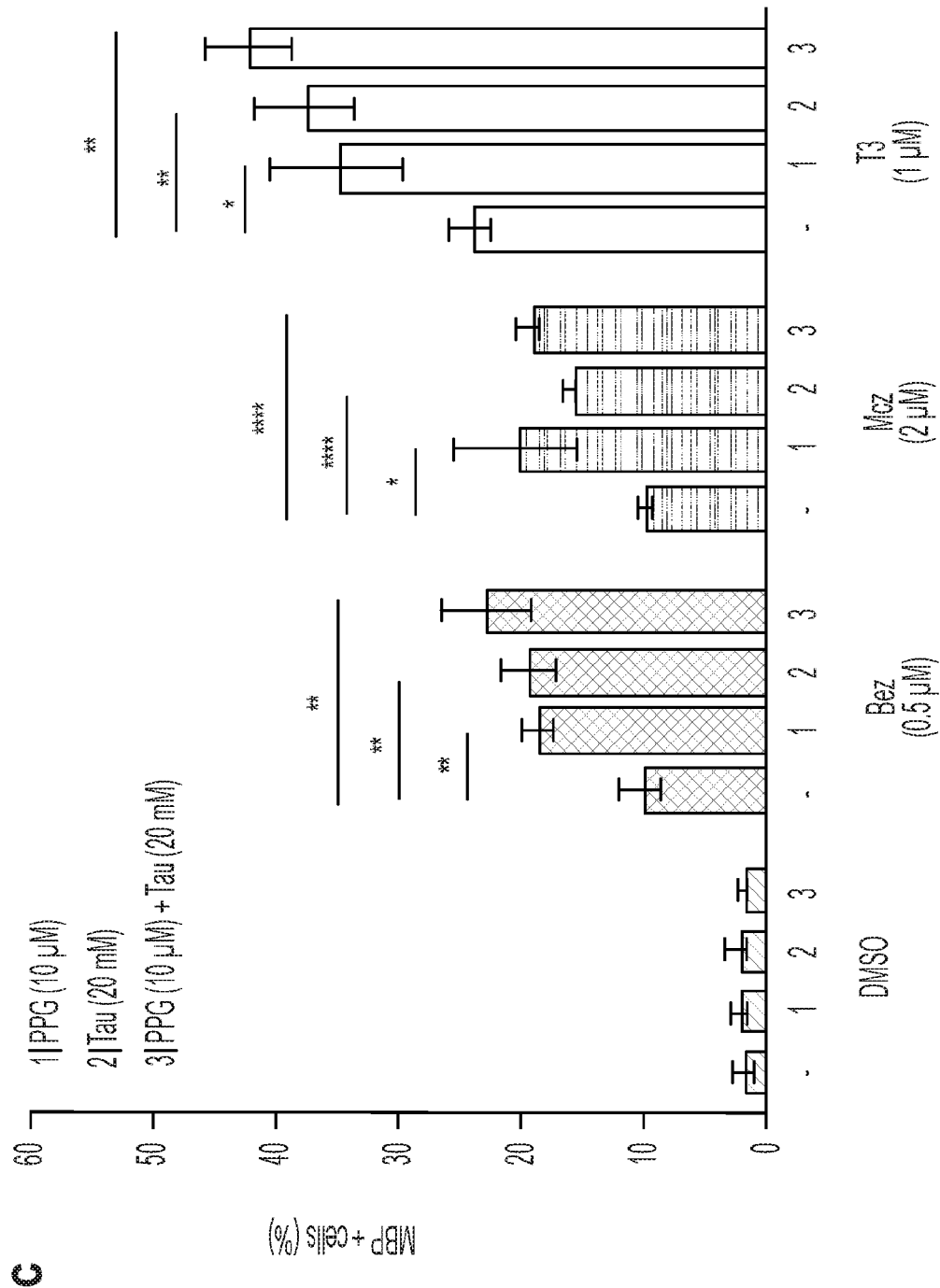

An alternative mechanism by which exogenously added taurine could enhance the process of drug-induced differentiation is by directly modulating the activity of a receptor or ion transporter, as described above, which serves to either stimulate or inhibit OL differentiation. Indeed, M1/M3 muscarinic receptor antagonism and the associated altered intracellular calcium levels is an essential component of the mechanism of benztropine- and clemastine-induced OPC differentiation (Deshmukh et al., Nature 502, 327-332, 2013; and Mei et al., Nat Med 20, 954-960, 2014). To determine if taurine itself contributes to the process of OPC differentiation, as opposed to indirect effects on redox state or mitochondrial health and cell viability, we inhibited endogenous taurine biosynthesis using propargylglycine (PPG). PPG is an irreversible inhibitor of cystathionine gamma-lyase, which can be used to inhibit the conversion of L-Cystathionine to L-Cysteine and downstream taurine biosynthesis in cells. Importantly, this also results in the inhibition of glutathione biosynthesis (FIG. 5b). The relative contribution of these two potential mechanisms could, therefore, be elucidated by adding either exogenous taurine or glutathione in combination with PPG. If taurine were to act by a mechanism involving direct modulation of the function of an essential protein, PPG treatment would inhibit oligodendrocyte differentiation and this effect could be rescued by exogenously adding back taurine. Similarly, if the OPC differentiation-enhancing activity of taurine was derived exclusively from a redox effect resulting from the combined activities of increased levels taurine and glutathione, PPG treatment would inhibit oligodendrocyte differentiation and this effect could be rescued by exogenously adding back reduced glutathione and/or other alternative biological reducing agents. However, paradoxically, PPG (10 μM) was found to significantly enhance the observed efficacy of all drug-induced differentiation conditions when added at either day 0 of day 3 (FIG. 5c, FIG. 14). Further, the magnitude of this effect was found to be similar to the effect of adding taurine itself to any given drug-induced differentiation condition, including T3 (FIG. 5c). Consistent with the effect of taurine addition, PPG had virtually no impact on differentiation efficiency under basal vehicle treated conditions. (FIG. 5c). Importantly, PPG was not found to impact overall survival in OPC cultures treated with DMSO, benztropine (0.5 μM) or miconazole (2 μM) (FIG. 14). In the case of T3 (1 μM) treatment, PPG (10 μM) was actually found to enhance overall cell number (FIG. 14). These observations make it unlikely that taurine itself stimulates a pro-differentiation process by directly interacting with a relevant receptor or alternative protein target, but rather that exogenous taurine enhances OL differentiation by serving as a feedstock to produce a limiting metabolite pool. Further, as PPG negatively impacts GSH biosynthesis, and as GSH and glutamate levels were found to be only minimally impacted by taurine supplementation (FIG. 5a, FIG. 13a-b), it is unlikely that a redox state effect is the primary mechanism contributing to the overall beneficial impact of taurine supplementation on OL differentiation and maturation.

Example 10. Some Exemplified Materials and Methods

Metabolites and small molecules. All the endogenous metabolites used in this study were from Sigma-Aldrich. Benztropine, miconazole and triiodothyronine (T3) were purchased from Sigma Aldrich (Saint Louis, Mo.). All the chemicals used in this study have a purity ≥95%.

Rat primary optic nerve OPCs were isolated by panning (>99% A2B5$^+$) and cultured in poly-D-lysine (10 μg/ml)-coated TC dishes in OPC culture media (Neurobasal Media, Invitrogen) supplemented with B27-without vitamin A (Invitrogen), 1× non-essential amino acids, 1× Glutamax, 1× anti-anti, β-mercaptoethanol and PDGF-AA (50 ng/ml; Peprotech) at 37° C. with 5% $CO_2$. The culture medium was replaced every 48 h and cells were collected before the confluency reached 60% to maintain a naive state. For differentiation, OPCs were plated at 1 million cells in one 10 cm petri-dish filled with differentiation media, which is identical to the culture media, but with PDGF-AA at 2 ng/ml. T3 and DMSO were used as the positive control and negative control, respectively. Five replicates of cells were collected at different times (0, 3, and 6 days) for metabolomics studies.

Global metabolomics and lipidomics. Cells incubated in differentiation medium were collected at Day 0, 3 and 6 for both the T3 and DMSO treated OPC. The cells were first rinsed with PBS twice to completely remove the culture medium and then scraped into a 1.5 mL Eppendorf vial using 500-1000 μL PBS. Subsequently, cells were collected by aspirating the supernatant after centrifugation at 1,000 rpm at 4° C. for 3 min. The global metabolites were extracted from cell pellets by a methanol:acetonitrile:water (2:2:1, v/v) solvent mixture. A volume of 600 μL of cold solvent was added to each pellet, vortexed for 30 s, and soaked in liquid nitrogen for 1 min. Samples were then allowed to thaw at room temperature and then sonicated for 10 min. This freeze-thaw process was repeated for additional twice. To further precipitate proteins, samples were incubated for 1 h at 20° C., followed by centrifugation at 16,000 g at 4° C. for 15 min. The protein concentration of the cells was measured in the final pellet after centrifugation using BCA assay. The resulting supernatant was removed and evaporated to dryness in a vacuum concentrator (LABCONCO CentriVap Benchtop). The dry extracts were then reconstituted in the appropriate volume of acetonitrile/water (1:1, v/v), normalized by the protein concentration with the lowest concentration approximately 50 μL, sonicated for 10 min, and centrifuged for 15 min at 16,000 g and 4° C. to remove insoluble debris. The supernatants were transferred to HPLC vials with inserts and stored at −80° C. prior to LC/MS analysis. The Folch method was used to extract the lipids from OPCs treated with T3 and DMSO for 6 days. A mixture of 600 μL, chloroform/MeOH (2:1, v/v) was used in the freeze-thaw extraction method as described above, and a subsequent addition of 600 μL, of water was performed. Using this liquid-liquid extraction method, the organic phase was collected, dried and finally reconstituted in IPA/MeOH/H$_2$O (5:1:4, v/v/v) before analysis.

Cell extracts were analyzed on a 6550 iFunnel QTOF mass spectrometer (Agilent Technologies) coupled with a 1290 UPLC system (Agilent Technologies). For global metabolomics, HPLC was carried out on a Luna Aminopropyl, 3 μm, 150 mm×1.0 mm I.D. HILIC column (Phenomenex). The mobile phase was composed of A=20 mM ammonium acetate and 40 mM ammonium hydroxide in 95% water (v/v) and B=95% acetonitrile. The remaining 5% components were either acetonitrile or water, respectively. A linear gradient from 100% B (0-5 min) to 100% A (50-55 min) was applied. A 10 min re-equilibration time was applied to the HILIC column for re-equilibration and maintenance of reproducibility. The flow rate was 50 μL/min, and the sample injection volume was 5 μL. ESI source conditions were set as follows: dry gas temperature, 200° C.; flow, 11 L/min, fragmentor, 380 V; sheath gas temperature, 300° C.; flow, 9 L/min; nozzle voltage, 500 V; capillary voltage, −500 V in ESI negative mode. The instrument was set to acquire data over the m/z range 50-1000, with the MS acquisition rate of 1 spectra/s. The sample sequence was randomized to avoid systematic decreases in signals over sample sets. For the MS/MS of selected precursors, the default isolation width was set as narrow (~1.3 m/z), with a MS acquisition rate at 2 spectra/s and MS/MS acquisition at 2 spectra/s to acquire over the m/z range 50-1000 and 25-1000; respectively. MS/MS data were acquired at the collision energy of 20 V.

For the lipidomics profiling, the separation was conducted using Agilent ZORBAX Eclipse Plus RRHD C18 column (2.1×100 mm, 1.8 μm). The mobile phase contains A (5:1:4 IPA/MeOH/H$_2$O with 5 mM NH$_4$O Ac and 0.1% CH$_3$COOH) and B (99:1 IPA/H$_2$O with 5 mM NH$_4$OAc and 0.1% CH$_3$COOH). The mobile phase starts with 0% B for 3 min and increases to 20% B in the following two minutes. The gradient gradually increases to 30% B until 25 mins and further to 95% B in next 10 mins, which is maintained for 2 mins. Subsequently, the mobile phase is set to the original 0% B (37-38 min) and another 10 min re-equilibration time was applied to for re-equilibration. The flow rate is 0.35 mL/min and the temperature kept at 50° C.

LC/MS data were converted to mzXML files using Masshunter Acquisition Software (Agilent Masshunter 6.0B). The mzXML files were uploaded to XCMS Online web platform for data processing (https://xcmsonline-.scripps.edu) including peak detection, retention time correction, profile alignment, and isotope annotation. Data were processed using both pair-wise and multigroup comparison, and the parameter settings were as follows: centWave for feature detection (Δm/z=15 ppm, minimum peak width=10 s, and maximum peak width=60 s); obiwarp settings for retention time correction (profStep=0.5); and parameters for chromatogram alignment, including mzwid=0.015, minfrac=0.5, and bw=5. The relative quantification of metabolite features was based on extracted ion chromatogram (EIC) areas. Paired parametric t-test and one-way ANOVA (post hoc Tukey test) were used to test the variation pattern of metabolite features between and across cell samples collected at different times after being treated with T3 and DMSO. Multiple group analysis and pairwise comparisons between DMSO and T3 at individual incubation time were conducted. The results output, including EICs, pairwise/multigroup cloud plot, multidimensional scaling plots, and principle components were exported directly from XCMS Online. Generally, the numbers of total pairwise comparison features and significantly altered features (statistically defined as $p<0.01$, including both upregulated and downregulated features) were reported in this study.

Targeted multiple pathway analysis. The metabolites in the upstream and downstream of taurine pathways are of great interest in this study. Due to the poor stability of several sulfur containing compounds including cysteine, GSH and GSSG, a different extraction method from the global metabolomics was developed and validated. Briefly, cell pellets were extracted with 150 μL 75% ACN in water modified with 0.1% formic acid using the freeze-thaw method mentioned above. The samples were further followed by centrifugation at 16,000 g and 4° C. for 15 min and the supernatant was directly injected into the Agilent triple-quad (QQQ, 6495). It was operated in multiple reaction monitoring mode (MRM), where the collision energies and product ions (MS2 or quantifier and qualifier ion transitions) were pre-optimized for each metabolite of interest (Table 1). Cycle time was 50 ms for each transition. ESI source conditions were set as following: gas temperature 250° C., gas flow 14 L/min, nebulizer 20 psi, sheath gas 250° C., sheath gas flow 11 L/min, capillary voltage 3000V, nozzle voltage 1500V and EMV 1000V in ESI positive mode. The analyses were performed on the Imtakt Amino Acid column (length 150×i.d. 2 mm, particle size 3 μm). The mobile phase was composed of A=50 mM ammonium formate in water (v/v) and B=100% acetonitrile in 0.1% formic acid. A linear gradient from 70% B (0-1 min) to 70% A (1-12 min, maintaining for 2 min) was applied. A 12 min re-equilibration time was applied to the column for re-equilibration. The flow rate was 200 μL/min, and the sample injection volume was 20 μL.

TABLE 1

The MRM transition of targeted metabolites in this study.

| Compound Name | Precursor Ion | Qualifier | Quantifier | Dwell (ms) | Fragmentor (V) | Collision Energy (V) |
|---|---|---|---|---|---|---|
| Cysteine sulfate | 202.0 | NA | 73.9 | 30 | 380 | 26 |
| Ascorbic acid | 177.0 | 140.9 | 95.0 | 30 | 380 | 2 |
| Cysteate | 170.0 | 106.1 | 123.9 | 30 | 380 | 14 |
| Taurocyamine | 168.0 | 59.0 | 125.9 | 30 | 380 | 14 |
| 3-Sulfino-L-alanine | 154.0 | 74.0 | 44.2 | 30 | 380 | 10 |
| Methionine | 150.1 | NA | 61.0 | 30 | 380 | 14 |
| Homocysteine | 136.0 | 56.1 | 90.1 | 30 | 380 | 10 |
| Creatine | 132.1 | 44.1 | 90.0 | 30 | 380 | 10 |

TABLE 1-continued

The MRM transition of targeted metabolites in this study.

| Compound Name | Precursor Ion | Qualifier | Quantifier | Dwell (ms) | Fragmentor (V) | Collision Energy (V) |
|---|---|---|---|---|---|---|
| Taurine | 126.0 | NA | 107.9 | 30 | 380 | 10 |
| L-Cysteine | 122.0 | 58.9 | 75.9 | 30 | 380 | 10 |
| Creatinine | 114.1 | 43.1 | 44.1 | 30 | 380 | 14 |
| hypotaurine | 110.0 | 48.0 | 91.9 | 30 | 380 | 6 |
| Serine | 106.1 | 42.1 | 60.1 | 30 | 380 | 10 |
| Cysteamine | 78.0 | NA | 61.0 | 30 | 380 | 14 |
| Glycine | 76.0 | 31.1 | 30.1 | 30 | 380 | 38 |
| GSSG | 613.2 | 355.0 | 483.9 | 30 | 380 | 18 |
| GSH | 308.1 | 76.0 | 84.0 | 30 | 380 | 46 |
| L-Cystine | 241.0 | 120.0 | 152.0 | 30 | 380 | 10 |
| L-Cystathionine | 223.1 | 88.0 | 134.0 | 30 | 380 | 10 |
| Creatine-phosphorous | 212.0 | 114.0 | 90.1 | 30 | 380 | 10 |

High content imaging. For dose-response co-treatment experiments, black, clear-bottom 384-well plates (Greiner) were coated with poly-D-lysine (10 µg ml$^{-1}$ in PBS). miconazole and benztropine were added at 8 doses in differentiation media; 3-fold dilutions down from 10 µM. taurine was then added at 8 concentrations; 3-fold dilutions down from 20 mM. This 384-well format was also utilized for experiments combining benztropine (0.5 µM), miconazole (2 µM) or T3 (1 µM) with propargylglycine (0.1, 3, 10, 30 µM), reduced glutathione (1, 10, 30, 100 µM) or ascorbic acid (1, 10, 30, 100 mM). OPCs were then seeded at a density of 1,000 cells per well, and the plates were incubated at 37° C. with 5% CO2 for 6 days. For time course experiments, cells were seeded at a density of 5,000 cells per well in poly-D-lysine-coated 96-well plates. Cells were treated with DMSO (0.1%), benztropine (0.5 µM), miconazole (2 µM) or T3 (1 µM) on day 0, and taurine (20 mM) was added in combination at 0, 1 or 3 days post-drug treatment. The plates were incubated at 37° C. with 5% CO2 for 6 days. On day 6, cells were then fixed for 20 min with 4% formaldehyde solution and stained with mouse anti-Myelin Basic Protein (MBP) antibody (MAB382, Millipore) or anti-A2B5 antibody (MAB312, Millipore) in 3% BSA, 0.3% Triton X-100 with overnight incubation at 4° C. The cells were washed and incubated with secondary antibody (goat anti-mouse Alexa Fluor488) and DAPI (Invitrogen) for 1 h at room temperature. The cells were washed and plates were sealed and imaged using an Opera confocal imaging reader (Perkin Elmer) or a Cellomics Cell Insight imaging reader (Thermo). An air ×10 lens was used to capture 9 images per well at both wavelengths (488 and 365 nm), with each image representing a different unique locations field in a single well. For image analysis, DAPI-stained nuclei and MBP-positive or A2B5-positive cell bodies were detected using an algorithm that selects for positive cell bodies and nuclei within a range of fluorescent emission values and sizes as determined by fitting parameters to positive (T3, 1 µM) and negative controls (DMSO, 0.1%). The numbers of DAPI-positive objects were enumerated in experiments where cell counts were required. Numerical results from the analyzed images were later exported for analysis using Excel (Microsoft) and/or Genedata software.

Cell viability analysis. In poly-D-lysine-coated white 384-well plates (Greiner), benztropine (0.5 µM), miconazole (2 µM) or T3 (1 µM) were added in combination with rotenone (0.1, 1, 3, 10 µM) or oligomycin (0.1, 1, 3, 10 µM). Cells were then seeded at a density of 1,000 cells per well, and the plates were incubated at 37° C. with 5% CO2 for 1, 3 or 6 days. At these three time points, the CellTiter-Glo Luminescent Cell Viability Assay (Promega) was utilized to analyze cytotoxicity.

Detection of caspase 3/7. In poly-D-lysine-coated white 96-well plates (Greiner), cells were seeded at 5,000 cells per well. Taurine (20 mM) was added on days 0 or 3, alone and in combination with benztropine (0.5 µM), miconazole (2 µM), T3 (1 µM) or Staurosporine (1 µM) added on day 0. The Caspase-Glo 3/7 Assay (Promega) was utilized to quantify caspase-3/7 activity 6, 24 and 48 h after drug and taurine addition on day 0. Caspase-3/7 activity was also measured 24, 48 and 72 h (days 4, 5 and 6) after taurine addition on day 3.

In vitro OL maturation assay. Cortical and hippocampal tissue was dissected from C57BL/6 mice at embryonic day 14 and dissociated in 0.5% Trypsin with 100 U/mL DNase I diluted in HBSS (+/+) for 10 min at 37° C. Reaction was stopped by supplementing to a final concentration of 10% v/v FBS, 100 µg/mL Soybean Trypsin Inhibitor and 10 U/mL DNase I. Cells were resuspended in plating media consisting of equal volumes of FCS, HBSS (+/+), High-Glucose DMEM with L-glutamine, and F-12 with L-glutamine, then plated onto acid pre-washed German glass coverslips coated with 50 µg/mL Poly-D-Lysine and 20 µg/mL Laminin at a density of 50,000 cells/cm$^2$. Cells were allowed to attach for 2 hrs and then coverslips were rinsed with PBS before being transferred to a 24-well plate containing 0.5 mL growth media consisting of: Neurobasal medium, B27 supplement (Gibco), 0.5× Glutamax (Thermo), 5 µg/mL gentamycin and 5 µM glutamic acid. Half of the cell media was replaced after 3 DIV with supplemental growth media not containing glutamic acid[47]. After 5 DIV, rat-derived cortical OPCs were added to the neuronal culture at a density of 5,000 cells/cm$^2$. Co-culture media used to resuspend and plate OPCs consisting of a 1:3 mixture of neuronal growth supplement (as above) and oligodendrocyte differentiation media, containing DMEM/F-12 (with L-glutamine), insulin-free N2 supplement, 1× Glutamax, 1×MEM non-essential amino acids, 1× β-mercaptoethanol, 2 ng/mL PDGF and 5 µg/mL gentamycin. All drugs and taurine co-treatment were added once to culture upon plating of OPCs at the following concentrations: 0.5 µM benztropine, 1.0 µM miconazole, each with or without 2 mM taurine. Cultures were maintained by replacing half of the media every three days, maintaining an equivalent concentration of taurine throughout in appropriate wells. Fourteen days after addition of OPC and drug treatments co-cultures were fixed for 15 min in 4% PFA and stained sequentially overnight with TUJ1

(rabbit; Covance) and MBP (chicken; AbCam) antibodies, each immediately followed by associated secondary antibodies Alexa488-Goat-anti-Rabbit (Thermo) and Cy3-Goat anti-Chicken (JacksonImmuno Research) and 1 µg/mL DAPI for nuclear counterstain. Immunostained coverslips were then invert mounted on glass slides using Fluoromount G (Southern Biotech). Randomly selected regions of 25 fields or greater were imaged at 63× magnification using a Zeiss 780 confocal microscope. Z-projection images were then rendered in Imaris (Bitplane) to identify apposition of oligodendrocyte and neuronal processes. Co-localization was quantified within regions of interest delineated as the periphery of individual oligodendrocytes. The co-localization index (adapted from a previously described method[48]) was calculated as total proportion of co-localized 3D surface area between Tuj1 (neuron) and oligodendrocyte (MBP) over total Tuj1 (neuronal process) area enclosed within each oligodendrocyte process tree as the selected region of interest (ROI, see FIG. 3B"). Mean colocalization values for each condition were normalized to the DMSO condition mean analyzed statistically using Prism software (GraphPad, v7) for two-way ANOVA comparisons (Drug Treatment×Taurine Supplement) with Tukey post-tests for statistical significance.

Statistical comparison of myelination in drug-treated co-cultures as well as drug-treated co-cultures with taurine supplement showed a significant main effect for benztropine (F(1,56)=27.82, p<0.0001) and taurine supplement (F(1,56)=10.8, p=0.0018), with significant Tukey post hoc results for benztropine alone vs. DMSO (q=3.19, p=0.0442), benztropine+taurine vs. DMSO (q=8.48, p<0.0001) and benztropine+taurine vs. benztropine alone (q=5.09, p=0.0037). Additionally, there was a significant main effect for miconazole treatment (F(1,46)=24.9, p<0.0001) and a main effect for taurine (F(1,46)=10.55, p<0.0022). Tukey post hoc tests showed no significant difference for miconazole alone vs. DMSO (q=3.61, p=0.065); however, there was a significant difference for miconazole+taurine vs. DMSO (q=8.24, p<0.0001) and miconazole+taurine vs. miconazole alone (q=4.54, p=0.0125). Taurine treatment alone showed no significant difference vs. DMSO in either benztropine or miconazole experiments (p=0.58 andp=0.54 respectively).

Western blot analysis. OPCs were plated in basal differentiation medium at 1.7×10⁵ cells/well and treated for 6 days with benztropine (0.5 µM), miconazole (2 µM) with and without the tested endogenous metabolites, T3 (1 µM) or DMSO. After washing with PBS, cells were collected in ice cold RIPA buffer containing protease and phosphatase inhibitors. Following incubation on ice for >20 min and sonication, lysed cells were centrifuged (16,000 g, 15 min at 4° C.). Total protein was quantified using a BCA analysis and 25 µg of protein from each sample was denatured by boiling with Bolt LDS Sample Buffer (4×) and Sample Reducing Agent (10×). Proteins were electrophoresed using Bolt 4-12% Bis-Tris gels (Life Technologies) and transferred to a PVDF membrane (Bio-Rad). The membrane was blocked with Odyssey PBS Blocking Buffer (LI-COR) and incubated overnight at 4° C. with anti-MBP (mouse, 1:2000) and anti-actin (mouse, 1:5000). Blots were incubated with HRP-conjugated secondary donkey anti-mouse antibody (LI-COR, 1:7500) and imaged using Odyssey CLx and Image Studio (LI-COR).

Mitochondrial respiration assay. Cellular oxygen consumption rate (OCR) was measured using an XFe96 extracellular flux analyzer (Seahorse Biosciences). OPCs were seeded at 40,000 cells/well in PLP-coated XFe96 plates and cultured for 6 days with taurine (2 and 20 mM) alone, or together with miconazole and benztropine. Cells were then incubated in assay medium (DMEM with 20 mM glucose, 5 mM pyruvate and 5 mM sodium bicarbonate, pH~7.4) for at least 30 min prior to the assay. Media to deliver a final assay well concentration corresponding to of 1 µM oligomycin, 2 µM carbonyl cyanide 4-(trifluoromethoxy) phenylhydrazone (FCCP) and 2 µM rotenone+2 µM antimycin A were pre-loaded into the compound delivery ports of the system. The assay starts with the recording of the basal OCR, followed by recording of the OCR in response to different compounds that constitute the Mitochondria Stress Test (Seahorse Biosciences, Agilent). Once the basal OCR was measured, the compounds were added sequentially and the effects on OCR measured 3 times every 5 min. Oligomycin blocks ATP synthase; FCCP dissipates the inner membrane potential enabling maximum electron flux through the electron transport chain (ETC); rotenone+antimycin A inhibit complexes I and III, respectively, thereby blocking the entry of electrons in the ETC and shutting down mitochondrial activity.

Statistical analysis. Unless otherwise stated, data represent mean±SD of representative experiments. Unless otherwise stated, statistical analysis was performed using Prism software (GraphPad, v7) for one-way ANOVA comparisons with Tukey post-tests for statistical significance.

It is understood that the examples and embodiments described herein are for illustrative purposes only and that various modifications or changes in light thereof will be suggested to persons skilled in the art and are to be included within the spirit and purview of this application and scope of the appended claims. Although any methods and materials similar or equivalent to those described herein can be used in the practice or testing of the present invention, the preferred methods and materials are described.

All publications, GenBank sequences, patents and patent applications cited herein are hereby expressly incorporated by reference in their entirety and for all purposes as if each is individually so denoted.

What is claimed is:

1. A method for treating or ameliorating one or more symptoms of a demyelinating disease in a subject, comprising administering to the subject (a) a pharmaceutical composition comprising a therapeutically effective amount of taurine or a taurine-like compound and (b) an agent that induces oligodendrocyte precursor cell (OPC) differentiation, thereby treating or ameliorating the symptoms of the demyelinating disease in the subject.

2. The method of claim 1, wherein the taurine or taurine-like compound is administered to the subject simultaneously with, prior to, or subsequent to administration of the agent that induces OPC differentiation.

3. The method of claim 1, wherein the taurine-like compound is an agent that can directly or indirectly upregulate the serine level in an OPC, pre-myelinating oligodendrocyte, or oligodendrocyte, thereby enhancing glycosphingolipid biosynthesis in the OPC, pre-myelinating oligodendrocyte, or oligodendrocyte.

4. The method of claim 1, wherein the taurine-like compound is a taurine precursor, a taurine metabolite, a taurine derivative, a taurine analog, or a substance required for taurine biosynthesis.

5. The method of claim 1, wherein the demyelinating disease is multiple sclerosis (MS).

6. The method of claim 1, wherein the subject is a human.

7. The method of claim 1, wherein the agent that induces OPC differentiation is a muscarinic receptor antagonist, a dopamine receptor antagonist, a histamine receptor antagonist, a beta adrenergic receptor modulator, or an opioid receptor modulator.

8. The method of claim 1, wherein the agent that induces OPC differentiation is benztropine, clemastine, miconazole, triiodothyronine (T3), or clobetasol .

9. The method of claim 1, further comprising administering to the subject a known agent for treating a demyelinating disease or a disease modifying drug.

10. The method of claim 9, wherein the known agent for treating a demyelinating disease is an S1P receptor agonist.

11. The method of claim 10, wherein the S1P receptor agonist is FTY720, MT1303, ACT-128800, BAF312, GSK2018682, CYM-5442, ONO-4641, AUY954, RG3477, SEW-2871, CS-0777, Syl930, AAL-R, RPC1063, RP-001, KRP-203, or CYM-5442.

12. The method of claim 9, wherein the known agent for treating a demyelinating disease or disease modifying drug is administered to the subject prior to, simultaneously with, or subsequent to administration of the pharmaceutical composition comprising a therapeutically effective amount of taurine or a taurine-like compoundi and/or the agent that induces OPC differentiation.

13. A method for increasing myelination in a subject, comprising administering to the subject (a) a pharmaceutical composition comprising a therapeutically effective amount of taurine or a taurine-like compound, and (b) an agent that induces OPC differentiation.

14. The method of claim 13, wherein the subject is a human.

15. The method of claim 13, wherein the pharmaceutical composition is administered to the subject simultaneously with, prior to, or subsequent to administration of the agent that induces OPC differentiation.

16. The method of claim 13, wherein the subject is afflicted with or is at risk of developing a demyelinating disease.

17. The method of claim 16, wherein the demyelinating disease is multiple sclerosis (MS).

18. A pharmaceutical composition, comprising (a) a therapeutically effective amount of taurine or a taurine-like compound and (b) one or more agents that induce OPC differentiation or treat a demyelinating disease.

19. The pharmaceutical composition of claim 18, further comprising a pharmaceutically acceptable carrier.

20. The pharmaceutical composition of claim 18, wherein the one or more agents that induce OPC differentiation or treat a demyelinating disease is benztropine, clemastine, miconazole, triiodothyronine (T3), clobetasol, or a S1P receptor agonist.

* * * * *